US011274146B2

(12) United States Patent
Song et al.

(10) Patent No.: US 11,274,146 B2
(45) Date of Patent: Mar. 15, 2022

(54) ANTI-C5A ANTIBODIES AND USES THEREOF

(71) Applicant: The Trustees of the University of Pennsylvania, Philadelphia, PA (US)

(72) Inventors: Wenchao Song, Bryn Mawr, PA (US); Sayaka Sato, Philadelphia, PA (US); Takashi Miwa, Bala Cynwyd, PA (US); Damodar Gullipalli, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 61 days.

(21) Appl. No.: 16/495,979

(22) PCT Filed: Mar. 23, 2018

(86) PCT No.: PCT/US2018/023927
§ 371 (c)(1),
(2) Date: Sep. 20, 2019

(87) PCT Pub. No.: WO2018/175833
PCT Pub. Date: Sep. 27, 2018

(65) Prior Publication Data

US 2020/0148754 A1 May 14, 2020

Related U.S. Application Data

(60) Provisional application No. 62/475,573, filed on Mar. 23, 2017.

(51) Int. Cl.
*C07K 16/18* (2006.01)
*C12N 15/85* (2006.01)

(52) U.S. Cl.
CPC .............. *C07K 16/18* (2013.01); *C12N 15/85* (2013.01); *C07K 2317/24* (2013.01); *C07K 2317/54* (2013.01); *C07K 2317/565* (2013.01); *C07K 2317/622* (2013.01); *C07K 2317/76* (2013.01); *C12N 2015/8518* (2013.01)

(58) Field of Classification Search
None
See application file for complete search history.

(56) References Cited

U.S. PATENT DOCUMENTS 6,355,245 B1 3/2002 Evans
6,987,166 B2 1/2006 Ward
7,432,356 B2 10/2008 Fung
2010/0285036 A1 11/2010 Smith
2011/0256154 A1 10/2011 Vincent
2012/0219524 A1 8/2012 Wong
2014/0314772 A1* 10/2014 Guo ........................ A61P 37/02 424/139.1
2016/0200805 A1 7/2016 Fung
2017/0002067 A1 1/2017 Guo
2017/0355756 A1* 12/2017 Julien ................... C12N 15/86

FOREIGN PATENT DOCUMENTS

| | | | |
|---|---|---|---|
| EA | 201291147 | | 8/2013 |
| EP | 1878441 | | 1/2008 |
| JP | 2005508889 | | 4/2005 |
| JP | 2013512209 | | 4/2013 |
| JP | 2013526861 | | 6/2013 |
| WO | WO 2008068048 | * | 6/2008 |
| WO | 2011137395 | | 11/2011 |
| WO | 2012027723 | | 3/2012 |
| WO | 2012088247 | | 6/2012 |
| WO | 2012112943 | | 8/2012 |
| WO | 2012145673 | | 10/2012 |
| WO | 2016005950 | | 1/2016 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Koenig "Mutational landscape of antibody variable domains reveals a switch modulating the interdomain conformational dynamics and antigen binding" PNAS E486-E495 (Year: 2017).*
International Preliminary Report on Patentability for PCT/US2018/023927 dated Sep. 24, 2019 (6 pages).
International Search Report for PCT/US2018/023927 dated Jul. 10, 2018 (5 pages).
Written Opinion of the International Searching Authorities for PCT/US2018/023927 dated Jul. 10, 2018 (5 pages).
Altshuler EP et al, "Generation of Recombinant Antibodies and Means for Increasing Their Affinity", 2010, Biochemistry (Moscow), 75:1584-1605.
Brown M et al., "Tolerance of Single, but not Multiple, Amino Acid Replacements in Antibody VH CDR2: A Means of Minimizing B Cell Wastage from Somatic Hypermutation?" 1996, J Immunol, 156:3285-3291.
Coiko R., Immunology: textbook, Moscow, publishing center "Academy", 2008, pp. 61-62.
Molines et al., "Strategies of Therapeutic Complement Inhibition", 2006, Molecular Immunology, 43:107-121.
Murray R et al., Harper's Biochemistry, 1988, 1:24-25.
Rudikoff et al., 1981, "Single Amino Acid Substitution Altering Antigen-binding Specificity", Proc. Natl. Acad. Sci., 79:1979-1983.

* cited by examiner

*Primary Examiner* — Adam Weidner
(74) *Attorney, Agent, or Firm* — Riverside Law LLP

(57) ABSTRACT

This invention relates to inhibition of the complement signaling using an anti-C5a antibody. Specifically, the invention relates to methods of treating a complement-mediated disease or complement-mediated disorder in an individual by contacting the individual with an anti-C5a antibody.

18 Claims, 7 Drawing Sheets

Specification includes a Sequence Listing.

A

Nucleic acid and amino acid sequences of VH of mAb 7A12. Signal peptide is underlined and CDR1, CDR2 and CDR3 sequences are bolded and highlighted in gray.

CATGGACTGAAGGAGTAGAAATCTTCAGTCCCTGAACACACTGACTGTAACA atggaatggagctgggtctctctcttcttcctgtcagtaactacaggtgtccactcccag

M E W S W V S L F F L S V T T G V H S Q gttcagctgcaacagtctgacgctgagttggtgaaacctggagcttcagtgaagatttcc

V Q L Q Q S D A E L V K P G A S V K I S tgcaaggtttctggctacaccttcactgaccatattattcactggatgaaccagaggcct

C K V S G Y T F T D H I I H W M N Q R P CDR1 (SEQ ID NO: 3)

gaacagggcctggaatggattggatatatttatcctagagatggtaatactaactacaat

E Q G L E W I G Y I Y P R D G N T N Y N CDR2 (SEQ ID NO: 4)

gaaaacttcaagggcaaggccacattgactgcagacaaatcctccagcacagcctacatg

E N F K G K A T L T A D K S S S T A Y M cagctcaacagcctgacatctgaggactctgcagtctatttctgtgcaagagaaaggaac

Q L N S L T S E D S A V Y F C A R E R N CDR3 (SEQ ID NO: 5)

ttggaatactttgactactggggccaaggcaccactctcacagtctcctcagccaaaacg

L E Y F D Y W G Q G T T L T V S S A K T acacccccatctgtctatccactggcc (SEQ ID NO: 1)

T P P S V Y P L A (SEQ ID NO: 2)

B

Nucleic acid and amino acid sequences of VL of mAb 7A12. Signal peptide is underlined and CDR1, CDR2 and CDR3 sequences are bolded and highlighted in gray.

CATGGACTGAAGGAGTAGAAAAAGCATCCTCTCATCTAGTTCTCAGAG atggagacagacacaatcctgctatgggtgctgctgctctgggttccaggctccactggt

M E T D T I L L W V L L L W V P G S T G gacattgtgctgacccaatctccagcttctttggctgtgtctctagggcagagggccacc

D I V L T Q S P A S L A V S L G Q R A T atctcctgcaaggccagccaaagtgttgattatgatggtgataattatatgaactggtac

I S C K A S Q S V D Y D G D N Y M N W Y CDR1 (SEQ ID NO: 8)

caacagaaaccaggacagccacccaaactcctcatctatgctgcatccaatctagattct

Q Q K P G Q P P K L L I Y A A S N L D S CDR2 (SEQ ID NO: 9)

gggatcccagccaggtttagtggcagtgggtctgggacagacttcaccctcaacatccat

G I P A R F S G S G S G T D F T L N I H cctgtggaggaagaagatgctgcaacctattattgtcagcaaagtaatgaggatccgtac

P V E E E D A A T Y Y C Q Q S N E D P Y CDR3 (SEQ ID NO: 10)

acgttcggaggggggaccaagctggaaataaaacgggctgatgctgcacca (SEQ ID NO: 6)

T F G G G T K L E I K R A D A A P (SEQ ID NO: 7)

Figure 7

ANTI-C5A ANTIBODIES AND USES THEREOF

CROSS-REFERENCE TO RELATED APPLICATION

This application is a U.S. national phase application filed under 35 U.S.C. § 371 claiming benefit to International Patent Application No. PCT/US2018/023927, filed Mar. 23, 2018, which is entitled to priority under 35 U.S.C. § 119(e) to U.S. Provisional Patent Application No. 62/475,573, filed Mar. 23, 2017, each of which applications is hereby incorporated herein by reference in its entirety.

STATEMENT REGARDING FEDERALLY SPONSORED RESEARCH OR DEVELOPMENT

This invention was made with government support under grant number AI044970awarded by the National Institutes of Health. The government has certain rights in the invention.

BACKGROUND OF THE INVENTION

The complement system is part of innate immunity that plays a key role in host defense. However, activated complement also has the potential to cause significant tissue injury and destruction and dysregulated complement activity has been found to be associated with a number of rare and common diseases such as paroxysmal nocturnal hemoglobinuria (PNH), atypical hemolytic uremic syndrome, rheumatoid arthritis, age-related macular degeneration, etc. Thus, anti-complement therapy is a promising way of treating these human disorders.

Complement C5 is a critical protein in the terminal pathway of complement activation and is the precursor protein for generating the potent pro-inflammatory mediator C5a, as well as the cytolytic membrane attack complex (MAC), C5b-9.

In some complement-mediated diseases, both C5a and MAC-mediated processes may contribute to pathogenesis, while in other diseases only C5a-mediated inflammation or MAC-mediated cellular injury may be involved. Since complement mediators, including C5a and MAC, also play an important role in host defense against pathogen infection, it is desirable that in therapeutic drug development, we develop anti-complement drugs that are selective, i.e. drugs that will block only the detrimental effect of complement in tissue injury while leaving its normal host defense function intact.

The hemolytic disease PNH is caused by MAC. Other anti-C5 mAbs for the treatment of PNH exist. However, those antibodies unnecessarily block C5a production, putting patients at a greater risk for infection than a therapeutic drug that blocks MAC alone. Likewise, there are complement-mediated diseases that may be mediated primarily by C5a-dependent inflammation (e.g., sepsis) and for such conditions, an anti-C5 mAb drug, while expected to be effective, would unnecessarily block MAC as a side effect.

Thus, there is a need in the art for anti-human C5a mAbs that can inhibit C5a-mediate activity but does not block MAC activity. The present invention addresses and meets these and other needs.

SUMMARY

In one embodiment, the present invention relates to an antibody that specifically binds to C5a. In one embodiment, the C5a is human C5a. In one embodiment, the antibody is a monoclonal antibody. In one embodiment, the antibody is a humanized antibody. In some embodiments, the antibody is a full-length antibody. In some embodiments, the antibody is an antibody fragment, which includes, but is not limited to, Fab, Fab', F(ab)2, F(ab')2, and scFv. In some embodiments, the antibody is part of a construct, for example a fusion construct comprising the antibody and a targeting moiety or an effector moiety. In some embodiments, the antibody is part of a conjugate construct, such as an antibody drug conjugate construct.

In one embodiment, the antibody is a chimeric antibody. In one embodiment, the antibody comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody comprises the CDRs: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In one embodiment, the antibody comprises a heavy chain comprising the amino acid sequence of SEQ ID NO:2, or a variant thereof. In one embodiment, the antibody comprises a light chain comprising the amino acid sequence of SEQ ID NO:7, or a variant thereof. In one embodiment, the antibody comprises a heavy chain comprising the amino acid sequence of SEQ ID NO:2, or a variant thereof and a light chain comprising the amino acid sequence of SEQ ID NO:7, or a variant thereof. In one embodiment, the antibody is 7A12.

In one embodiment, the present invention relates to a method of treating a complement pathway-mediated disease or disorder in an individual, comprising the step of administering to said individual the anti-C5a antibody described herein. In one embodiment, the disease or disorder is at least selected from the group consisting of: macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, autoimmune hemolytic anemia (AIHA), Gaucher disease, myasthenia gravis, neuromyelitis optica, (NMO), multiple sclerosis, delayed graft function, antibody-mediated rejection, atypical hemolytic uremic syndrome (aHUS), central retinal vein occlusion (CRVO), central retinal artery occlusion (CRAO), epidermolysis bullosa, sepsis, septic shock, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, graft versus host disease (GVHD) or any combinations thereof. In some embodiments, the AP-mediated disease is sepsis, septic shock, rheumatoid arthritis, autoimmune hemolytic anemia, GvHD, anti-phospholipid syndrome, or Gaucher's disease. In one embodiment, administration of the anti-C5a antibody inhibits the activity of a C5a protein.

In one embodiment, the present invention relates to a method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 3, SEQ ID NO: 4, SEQ ID NO: 5, SEQ ID NO: 8, SEQ ID NO: 9, and SEQ ID NO: 10, or a variant or variants thereof. In one embodiment, the antibody is an antibody fragment selected from the group consisting of a Fab, Fab', F(ab)2, F(ab')2, scFv, and combinations thereof.

In one embodiment, the present invention describes an antibody against human C5a, wherein the antibody has a heavy chain variable (vH) region that has an amino acid sequence that is more than about 90% (such as more than any of 91%, 92%, 93%, 94%, 95%, 96%, 97%, 98%, 99%, or 100%) identical to SEQ ID NO: 2, or a variant thereof. In one embodiment, the antibody is an antibody fragment selected from the group consisting of a Fab, Fab', F(ab)2, F(ab')2, scFv, and combinations thereof.

In one embodiment, the present invention describes an antibody against human C5a, wherein the antibody has a light chain variable (vL) region that has an amino acid sequence that is more than about 90% (such as more than any of 91%, 92%, 93%, 94%, 95%, 96%, 97%, 98%, 99%, or 100%) identical to SEQ ID NO: 7, or a variant thereof. In one embodiment, the antibody is an antibody fragment selected from the group consisting of a Fab, Fab', F(ab)2, F(ab')2, scFv, and combinations thereof.

In one embodiment, the present invention is an antibody against human C5a, wherein the antibody has a heavy chain variable (vH) region and a light chain variable (vL) region, wherein the vH region has an amino acid sequence that is more than about 90% (such as more than any of 91%, 92%, 93%, 94%, 95%, 96%, 97%, 98%, 99%, or 100%) identical to SEQ ID NO: 2, or a variant thereof, and wherein the vL region has an amino acid sequence that is more than about 90% (such as more than any of 91%, 92%, 93%, 94%, 95%, 96%, 97%, 98%, 99%, or 100%) identical to SEQ ID NO: 7, or a variant thereof. In one embodiment, the antibody is an antibody fragment selected from the group consisting of a Fab, Fab', F(ab)2, F(ab')2, scFv, and combinations thereof.

In one embodiment, the present invention is a cell comprising at least one the antibodies described elsewhere herein. In one embodiment, the cell produces at least one of the antibodies described elsewhere herein. In one embodiment, the cell is a hybridoma.

In one embodiment, the present invention is a cell line comprising at least one of the antibodies described herein. In one embodiment, the cell line produces at least one of the antibodies described herein. In one embodiment, the cell line is a hybridoma cell line.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings. In the drawings:

FIG. 1A and FIG. 1B, depicts results demonstrating that mAb 7A12 binds to human C5. FIG. 1A depicts reactivity of 7A12 and 2G1, a control anti-C5 mAb, with intact human C5 as assessed by ELISA. The plate was coated with purified human C5. After incubation with serially diluted 7A12 or control anti-C5 mAb, bound mAb was detected by HRP-conjugated rabbit anti-mouse IgG. Both 7A12 and the control anti-C5 mAb showed high reactivity with human C5. FIG. 1B depicts by western-blotting, that mAb 7A12 and the control anti-C5 mAb recognized purified human C5 protein under non-reducing and reducing conditions, respectively. The observed 7A12-reactive 190 kDa band represents the whole C5 protein, whereas the 115 kDa band represents the C5 α-chain. NR: non-reducing condition; R: reducing condition.

FIG. 3A and FIG. 3B, depicts results showing that unlike the control anti-C5 mAb 2G1 that does not bind C5a, 7A12 binds human C5a in a dose-dependent manner, but it does not bind mouse C5a. A plate was coated with human C5a or mouse C5a. After incubation with serially diluted 7A12 or the control anti-C5 mAb, bound mAb was detected by HRP-conjugated rabbit anti-mouse IgG. FIG. 3A depicts that mAb 7A12 showed high reactivity to human C5a. Since mAb 7A12 reacts with the whole C5 protein (as shown in FIG. 1), it can be concluded that mAb 7A12 binds both the C5a moiety of native human C5 and free human C5a. On the other hand, no binding of the control anti-C5 mAb to human C5a was seen. FIG. 3B depicts that binding of mAb 7A12 to C5a was specific to human C5a with little binding to mouse C5a.

FIG. 4A and FIG. 4B, depicts the results of experiments assessing the binding affinity of mAb 7A12 to human C5 and C5a. Purified human C5 or C5a was coupled onto CM4 chip using the amine coupling method. Biacore analysis was performed on a Biacore-2000 instrument. The chip was regenerated between each binding using 50 mM NaOH. mAb 7A12 binds to human C5, depicted in FIG. 4A, and human C5a, depicted in FIG. 4B with similar affinities.

FIG. 6A through FIG. 6D, depicts results demonstrating that mAb 7A12, but not the control anti-C5 mAb 2G1, inhibits C5a-induced intracellular calcium mobilization in U937 cells. No calcium mobilization occurred in U937 cells expressing the human C5a receptor (U937-C5aR) in the absence of human C5a stimulation, shown in FIG. 6A. C5a (10 nM) treatment led to a transient calcium influx in U937-C5aR cells, shown in FIG. 6B, which could be inhibited by pre-incubation with mAb 7A12 (50 μg/ml), shown in FIG. 6C, but not with the control anti-C5 mAb 2G1 (50 μg/ml), shown in FIG. 6D. Arrows refer to the time point when C5a or a mixture of C5a and antibody was added to the cell suspension.

FIG. 7, comprising FIG. 7A and FIG. 7B, depicts sequences of the variable regions of mAb 7A12 heavy and light chains. FIG. 7A depicts nucleic acid and amino acid sequences of VH of mAb 7A12. Signal peptide is underlined and CDR1, CDR2 and CDR3 sequences are bolded and highlighted in gray. FIG. 7B depicts nucleic acid and amino acid sequences of VL of mAb 7A12. Signal peptide is underlined and CDR1, CDR2 and CDR3 sequences are bolded and highlighted in gray.

DETAILED DESCRIPTION OF THE INVENTION

Figure 1:
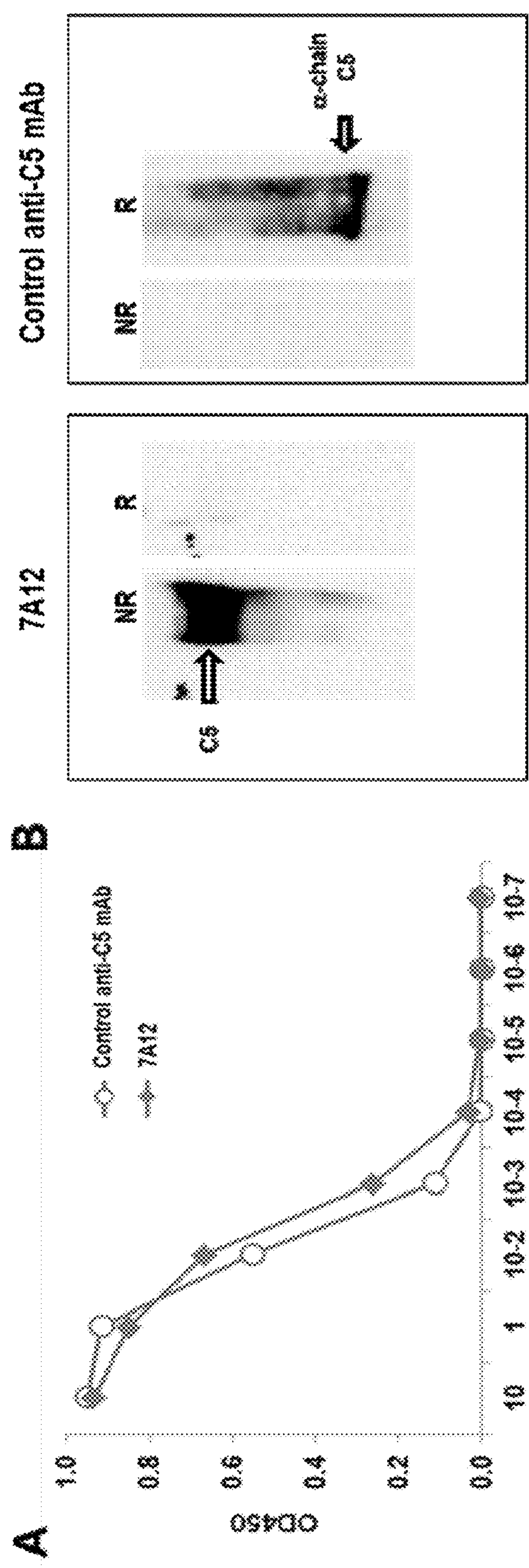
FIG. 1, comprising

This invention relates to the inhibition of complement signaling using an anti-C5a antibody. In various embodiments, the invention is directed to compositions and methods for treating a complement-mediated disease or complement-mediated disorder in an individual by contacting the individual with an anti-C5a antibody. The complement-mediated diseases and disorders that can be treated with the compositions and methods of the invention include, but are not limited to, macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, autoimmune hemolytic anemia (AIHA), Gaucher disease, myasthenia gravis, neuromyelitis optica, (NMO), multiple sclerosis, delayed graft function, antibody-mediated rejection, atypical hemolytic uremic syndrome (aHUS), central retinal vein occlusion (CRVO), central retinal artery occlusion (CRAO), epidermolysis bullosa, sepsis, septic shock, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, graft versus host disease (GVHD) or any combinations thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "inhibit" and "inhibition," as used herein, means to reduce, suppress, diminish or block an activity or function by at least about 10% relative to a control value. In some embodiments, the activity is suppressed or blocked by at least about 50% compared to a control value. In some embodiments, the activity is suppressed or blocked by at least about 75%. In some embodiments, the activity is suppressed or blocked by at least about 95%.

The terms "effective amount" and "pharmaceutically effective amount" refer to a sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The terms "patient," "subject," "individual," and the like are used interchangeably herein, and refer to any animal, in some embodiments a mammal, and in some embodiments a human, having a complement system, including a human in need of therapy for, or susceptible to, a condition or its sequelae. The individual may include, for example, dogs, cats, pigs, cows, sheep, goats, horses, rats, monkeys, and mice and humans.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Operably linked" or "operatively linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "therapeutic treatment" is a treatment administered to a subject who exhibits signs of disease or disorder, for the purpose of diminishing or eliminating those signs.

As used herein, "treating a disease or disorder" means reducing the frequency and/or severity of a sign and/or symptom of the disease or disorder is experienced by a patient.

The phrase "biological sample", "sample" or "specimen" as used herein, is intended to include any sample comprising a cell, a tissue, or a bodily fluid in which expression of a nucleic acid or polypeptide can be detected. The biological sample may contain any biological material suitable for detecting the desired biomarkers, and may comprise cellular and/or non-cellular material obtained from the individual. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "antibody," as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from a subject with heavy chain disease, or prepared by the cloning and expression of VH (variable heavy chain immunoglobulin) genes from a subject.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments, a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883. The skilled artisan will understand that there are multiple methods and techniques used for predicting CDR sequences. Thus, the CDR sequences of a given antibody can vary somewhat depending on which methods and techniques are employed to predict the CDR sequences. Exemplary methods and techniques include, but are not limited to, those described in Lyskov et al., 2013, PLoS One, 8(5): e63906; Kunik, et al., 2012, Nucleic Acids Res. 40:W521-524; Marcatili et al., 2008, Bioinformatics 24:1953; Chothia et al., 1989, Nature 342:887; Kabat et al., 1991, Sequences of Proteins of Immunological Interest, 5th Ed. Public Health Service, National Institutes of Health, Bethesda, Md.; Johnson et al., 2000, Nucleic Acids Res 28:214; Martin et al., 1989, P.N.A.S 86:9268; MacCallum et al., 1996, J Mol Biol 5:732; and Dunbar et al., 20106, Nucleic Acids Res. 44:W474-478.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes and binds to a specific target molecule, but does not substantially recognize or bind other molecules in a sample. In some instances, the terms "specific binding" or "specifically binding," is used to mean that the recognition and binding is dependent upon the presence of a particular structure (e.g., an antigenic determinant or epitope) on the target molecule. If, for example, an antibody specifically binds to epitope "A," the presence of an unlabelled molecule containing epitope A (or free, unlabeled A) in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and or at least about 75%, or at least about 90%, or at least about 95% of the nucleotide residues of the first portion are capable of base pairing with nucleotide residues in the second portion. In some embodiments, all nucleotide residues of the first portion are capable of base pairing with nucleotide residues in the second portion.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

"Isolated" means altered or removed from the natural state. For example, a nucleic acid or a peptide naturally present in its normal context in a living subject is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "progeny" as used herein refers to a descendent or offspring and includes the offspring of a mammal, and also included the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. In various embodiments, the variant sequence is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to the reference sequence.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "scanning window," as used herein, refers to a segment of a number of contiguous positions in which a sequence may be evaluated independently of any flanking sequence. A scanning window generally is shifted incrementally along the length of a sequence to be evaluated with each new segment being independently evaluated. An incremental shift may be of 1 or more than one position.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

This invention relates to the inhibition of the complement signaling and complement-related diseases and disorders using an anti-C5a antibody. In one embodiment, the invention is directed to inhibiting the complement signaling cascade by specifically targeting the complement component C5 and its cleavage product C5a protein, while leaving C5 cleavage product C5b functional. In one embodiment, the invention is directed to methods of treating and preventing inflammation and autoimmune diseases and disorders mediated by unwanted, uncontrolled, or excessive complement activation. In one embodiment, the invention is directed towards the treatment of a complement-mediated disease or a complement-mediated disorder in an individual by contacting the individual with an anti-C5a antibody. In some embodiments, the invention is directed to methods of treating C5a-mediated chemotaxis while leaving C5b-mediated MAC assembly intact.

In one embodiment, the invention is a method of treating a complement-mediated disease or disorder in an individual, comprising the step of administering to said individual an anti-C5a antibody, thereby selectively inhibiting the effects of C5a protein. Examples of complement-mediated diseases and disorders that can be treated using the methods of the invention include, but are not limited to macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, autoimmune hemolytic anemia (AIHA), Gaucher disease, myasthenia gravis, neuromyelitis optica, (NMO), multiple sclerosis, delayed graft function, antibody-mediated rejection, atypical hemolytic uremic syndrome (aHUS), central retinal vein occlusion (CRVO), central retinal artery occlusion (CRAO), epidermolysis bullosa, sepsis, septic shock, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, graft versus host disease (GVHD) or any combinations thereof. In some embodiments, the AP-mediated disease is sepsis, septic shock, rheumatoid arthritis, autoimmune hemolytic anemia, GvHD, anti-phospholipid syndrome, or Gaucher's disease.

The ability of the immune system to discriminate between "self" and "non-self" antigens is vital to the functioning of the immune system as a specific defense against invading microorganisms. "Non-self" antigens are those antigens on substances entering or present in the body which are detectably different or foreign from the subject's own constituents, whereas "self" antigens are those which, in the healthy subject, are not detectably different or foreign from its own constituents. In various embodiments of the methods, the complement activation that is inhibited is that which was triggered by at least one of the group consisting of a microbial antigen, a non-biological foreign surface, altered self-tissue, or combinations thereof. One example of a non-biological foreign surface is blood tubing such as that used in cardio-pulmonary bypass surgery or kidney dialysis. Examples of altered self-tissues include apoptotic, necrotic and ischemia-stressed tissues and cells, or combinations thereof.

In some embodiments, the anti-C5a antibodies of the invention inhibit the downstream effects of activation of the alternative complement pathway (AP), the classical pathway (CP), or the lectin pathway (LP). Generally, the CP is initiated by antigen-antibody complexes, the LP is activated by binding of lectins to sugar molecules on microbial surfaces, while the AP is constitutively active at a low level but can be quickly amplified on bacterial, viral, and parasitic cell surfaces due to the lack of regulatory proteins. Host cells are usually protected from AP complement activation by regulatory proteins. But in some situations, such as when the regulatory proteins are defective or missing, the AP can also be activated uncontrollably on host cells, leading to complement-mediated disease or disorder. The CP consists of components C1, C2, C4 and converges with the AP at the C3 activation step. The LP consists of mannose-binding lectins (MBLs) and MBL-associated serine proteases (Masps) and shares with the CP the components C4 and C2. The AP consists of components C3 and several factors, such as factor B, factor D, properdin, C5 and the fluid phase regulator factor H. Complement activation consists of three stages: (a) recognition, (b) enzymatic activation, and (c) membrane attack leading to cell death. The first phase of CP complement activation begins with C1. C1 is made up of three distinct proteins: a recognition subunit, C1q, and the serine protease subcomponents, C1r and C1s, which are bound together in a calcium-dependent tetrameric complex, C1r2 s2. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, C4b2a, which in turn cleaves C3 to form C3a and C3b. Activation of the LP is initiated by MBL binding to certain sugars on the target surface and this triggers the activation of MBL-associated serine proteases (MASPs) which then cleave C4 and C2 in a manner analogous to the activity of C1s of the CP, resulting in the generation of the C3 convertase, C4b2a. Thus, the CP and LP are activated by different mechanisms but they share the same components C4 and C2 and both pathways lead to the generation of the same C3 convertase, C4b2a. The cleavage of C3 by C4b2a into C3b and C3a is a central event of the complement pathway for two reasons. It initiates the AP amplification loop because surface deposited C3b is a central intermediate of the AP. Both C3a and C3b are biologically important. C3a is proinflammatory and together with C5a are referred to as anaphylatoxins. C3b and its further cleavage products also bind to complement receptors present on neutrophils, eosinophils, monocytes and macrophages, thereby facilitating phagocytosis and clearance of C3b-opsonized particles. Finally, C3b can associate with C4b2a to form the C5 convertase of the CP and LP to activate the terminal complement sequence, leading to the production of C5a, a potent proinflammatory mediator, and the assembly of the lytic membrane attack complex (MAC), C5-C9.

In one embodiment, the activity of the complement pathway that is inhibited using a method of the invention is complement pathway activation induced by at least one of the group selected from a lipopolysaccharide (LPS), lipooligosaccharide (LOS), pathogen-associated molecular patterns (PAMPs) and danger-associated molecular patterns (DAMPs). In another embodiment, the activity of complement signaling that is inhibited using a method of invention is the activity of C5a protein. In another embodiment, the activity of the complement pathway that is inhibited using a method of the invention is C5a dependent.

In one embodiment, the invention is a method of inhibiting initiation of an inflammatory cascade through terminal complement activation in an individual, comprising the step of administering to said individual an anti-C5a antibody, thereby inhibiting initiation of C5a-dependent inflammation through terminal complement activation originating from CP, LP or AP activation in an individual. Examples of these embodiments are sepsis patients who suffer from complement-mediated systemic inflammation and individuals suffering from conditions that may be caused by complement-mediated, organ-specific inflammation such as aHUS, AIHA, anti-phospholipid syndrome, GVHD, asthma, ischemic/reperfusion injury, rheumatoid arthritis and ANCA-mediated kidney diseases. In various embodiments of the invention, diseases and disorders that can be treated using the compositions and methods of the invention include, but are not limited to, complement-mediated hemolysis, complement-mediated aHUS, C3 glomerulopathy, neuromyelitis optica, myasthenia gravis, asthma, ischemic/reperfusion injury, sepsis, septic shock, rheumatoid arthritis and ANCA-mediated kidney diseases or disorders. In some embodiments, the AP-mediated disease is sepsis, septic shock, rheumatoid arthritis, autoimmune hemolytic anemia, GvHD, anti-phospholipid syndrome, or Gaucher's disease.

In various other embodiments, provided herein are methods of identifying a potential anti-C5a antibody having inhibitory effects on complement signaling. One such method includes the steps of: a) stably transfecting cells with the C5a receptor; b) seeding the cells, in chemotaxis assay buffer (RPMI media with 0.5% BSA) onto the upper chambers of Transwell inserts; c) adding 10 nM of recombinant human complement C5a pretreated with antibody in the chemotaxis assay buffer; d) incubating for 3 hours at 37° C.; e) collecting the migrated cells from the lower chambers and counting the cells using a Coulter counter; f) comparing the number of cells seeded in the that migrated into the lower chamber Transwells that received recombinant human complement C5a to the number of cells that migrated into the lower chamber of a positive comparator control Transwell and a negative comparator control Transwell; wherein when the number of migrated cells is diminished as compared with the positive comparator control, the anti-C5a antibody is identified.

In various other embodiments, provided herein are methods of identifying a potential anti-C5a antibody having inhibitory effects on complement signaling. One such method includes the steps of: a) stably transfecting cells with the C5a receptor; b) washing cells with calcium mobilization assay HEPES buffer (25 mM HEPES, 119 mM NaCl, 5 mM KCl, 5.6 mM glucose, 0.4 mM $MgCl_2$, and 1 mM $CaCl_2$) containing 1 mg/ml bovine serum albumin (BSA); c) incubating the cells with 1 μM indo-1 acetoxymethyl ester at room temperature for 30 minutes; d) washing cells twice and resuspending in 1.3 mL of above mentioned buffer; e) mixing 10 nM human C5a protein and 50 μg/ml C5a antibody to a final concentration of 10 nM of protein and 50 μg/ml of antibody at room temperature; f) measuring intercellular $Ca^{2+}$ at an excitation wavelength of 360 nm and an emission wavelength of 415 nm using an Infinite F200 multimode microplate reader; g) comparing the C5a-induced intercellular calcium mobilization in cells treated with of a positive comparator control and a negative comparator control; wherein when the calcium mobilization is diminished as compared with the positive comparator control, the anti-C5a antibody is identified.

Anti-C5a Antibodies

In some embodiments, the invention includes compositions comprising an antibody that specifically binds to C5 and C5a. In one embodiment, the anti-C5a antibody of the invention specifically binds to C5. In one embodiment, the anti-C5a antibody of the invention specifically binds to C5a. In one embodiment, the anti-C5a of the invention, specifically binds to both C5 and C5a. In one embodiment, the anti-C5a of the invention, specifically binds both to the C5a moiety of C5 and to free C5a. In some embodiments, the anti-C5a antibody of the invention specifically binds to C5, but does not block C5 cleavage into C5a and C5b. In one embodiment, the anti-C5a antibody is a polyclonal antibody. In another embodiment, the anti-C5a antibody is a monoclonal antibody. In some embodiments, the anti-C5a antibody does not block C5 cleavage into C5a and C5b but inhibits C5a-dependent biological activity. In some embodiments, the anti-C5a antibody is a chimeric antibody. In further embodiments, the anti-C5a antibody is a humanized antibody. In some embodiments, the antibody is an antibody fragment. In some embodiments, the C5a is human C5a.

In some embodiments, binding of the antibody or the fragment of the antibody to human C5a is associated with a reduction in the expression level or half-life of C5a in an intact organism. In some embodiments, the invention is a protein or a polypeptide capable of binding to human C5a. In some embodiments, the antibody or antibody fragment, the protein, or the polypeptide binds to a relevant portion or fraction or epitope of the human C5a, and the binding of the antibody, or the antibody fragment thereof, or the protein or the polypeptide to the relevant portion of the human C5a is associated with a reduction in the expression level or half-life of C5a in an intact organism.

In some embodiments, binding of the antibody or the fragment of the antibody to human C5a is associated with a reduction in the activity of C5a in the complement activation pathway in an intact organism. In some embodiments, the invention is a protein or a polypeptide capable of binding to human C5a. In some embodiments, the antibody or antibody fragment, the protein or the polypeptide binds to a relevant portion or fraction or epitope of the human C5a; and the binding of the antibody, or the antibody fragment thereof, or the protein or the polypeptide to the relevant portion of the human C5a is associated with a reduction in the activity of C5a in an intact organism.

In some embodiments, the human C5a binding antibody or a C5a binding antibody fragment thereof, is further conjugated to a protein, a peptide or another compound. In some embodiments, the C5a binding antibody, or an antibody fragment thereof, is conjugated to a protein, a peptide or other compound. In some embodiments, the protein, peptide or other compound to which the human-C5 binding antibody or antibody fragment thereof is conjugated is a targeting moiety (i.e., the targeting moiety specifically binds to a molecule other than C5a). In some embodiments, the protein, peptide, or other compound to which the C5a binding antibody or antibody fragment thereof is conjugated to is an effector molecule (e.g., a cytotoxic molecule).

In one embodiment, the anti-C5a antibody or an antigen-binding fragment thereof comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof. In another embodiment, the anti-C5 antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10, or a variant or variants thereof.

In some embodiments, the anti-C5a antibody or antigen-binding fragment thereof comprises: VH-CDR1 comprising the amino acid sequence of SEQ ID NO:3 or a variant thereof comprising up to about 3 (such as about any of 1, 2, or 3) amino acid substitutions; and VL-CDR1: SEQ ID NO:8, or a variant thereof comprising up to about 3 (such as about any of 1, 2, or 3) amino acid substitutions. In some embodiments, the anti-C5a antibody or an antigen-binding fragment thereof comprises: VH-CDR1 comprising the amino acid sequence of SEQ ID NO:3; and VL-CDR1: SEQ ID NO:8.

In some embodiments, the anti-C5a antibody or antigen-binding fragment thereof comprises: VH-CDR2 comprising the amino acid sequence of SEQ ID NO:4, or a variant thereof comprising up to about 3 (such as about any of 1, 2, or 3) amino acid substitutions; and VL-CDR2: SEQ ID NO:9, or a variant thereof comprising up to about 3 (such as about any of 1, 2, or 3) amino acid substitutions. In some embodiments, the anti-C5a antibody or an antigen-binding fragment thereof comprises: VH-CDR2 comprising the amino acid sequence of SEQ ID NO:4; and VL-CDR2: SEQ ID NO:9.

In some embodiments, the anti-C5a antibody or antigen-binding fragment thereof comprises: VH-CDR3 comprising the amino acid sequence of SEQ ID NO:5, or a variant thereof comprising up to about 3 (such as about any of 1, 2, or 3) amino acid substitutions; and VL-CDR3: SEQ ID NO:10, or a variant thereof comprising up to about 3 (such as about any of 1, 2, or 3) amino acid substitutions. In some embodiments, the anti-C5a antibody or an antigen-binding fragment thereof comprises: VH-CDR3 comprising the amino acid sequence of SEQ ID NO:5; and VL-CDR3: SEQ ID NO:10.

In some embodiments, the anti-C5a antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5, or a variant thereof comprising up to about 3 (such as about any of 1, 2, or 3) amino acid substitutions; VL-CDR1 comprising the amino acid sequence of SEQ ID NO: 8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10, or a variant thereof comprising up to about 3 (such as about any of 1, 2, or 3) amino acid substitutions.

In some embodiments, the anti-C5a antibody or antigen-binding fragment thereof comprises: VH-CDR1 comprising the amino acid sequence of SEQ ID NO:3, or a variant thereof comprising up to about 3 (such as about any of 1, 2, or 3) amino acid substitutions; VH-CDR2 comprising the amino acid sequence of SEQ ID NO:4, or a variant thereof comprising up to about 3 (such as about any of 1, 2, or 3) amino acid substitutions; VH-CDR3 comprising the amino acid sequence of SEQ ID NO:5; VL-CDR1 comprising the amino acid sequence of SEQ ID NO:8, or a variant thereof comprising up to about 3 (such as about any of 1, 2, or 3) amino acid substitutions; VL-CDR2 comprising the amino acid sequence of SEQ ID NO:9, or a variant thereof comprising up to about 3 (such as about any of 1, 2, or 3) amino acid substitutions; and VL-CDR3 comprising the amino acid sequence of SEQ ID NO:10.

In some embodiments, the anti-C5a antibody or antigen-binding fragment thereof comprises: VH-CDR1 comprising the amino acid sequence of SEQ ID NO:3; VH-CDR2 comprising the amino acid sequence of SEQ ID NO:4; VH-CDR3 comprising the amino acid sequence of SEQ ID NO:5; VL-CDR1 comprising the amino acid sequence of SEQ ID NO:8; VL-CDR2 comprising the amino acid sequence of SEQ ID NO:9; and VL-CDR3 comprising the amino acid sequence of SEQ ID NO:10.

In some embodiments, the anti-C5a antibody or an antigen binding fragment thereof comprises a heavy chain comprising the amino acid sequence of SEQ ID NO:2, or a variant thereof. In other embodiments, the anti-C5a antibody comprises a light chain comprising the amino acid sequence of SEQ ID NO:7, or a variant thereof. In another embodiment, the anti-C5a antibody is a monoclonal antibody designated mAb 7A12. The monoclonal anti-C5a antibody designated mAb 7A12 comprises a heavy chain comprising the amino acid sequence of SEQ ID NO:2, or a variant thereof, and a light chain comprising the amino acid sequence of SEQ ID NO:7, or a variant thereof. In some embodiments, the monoclonal anti-C5a antibody is a humanized antibody having one or more or all of the CDRs, or variants thereof, of the mAb designated 7A12. In some embodiments, the monoclonal anti-C5a antibody is a chimeric antibody having one or more or all of the CDRs, or variants thereof, of the mAb designated 7A12.

In some embodiments, the anti-C5a antibody or an antigen binding fragment thereof comprises at least one of CDR1, CDR2, and CDR3 of the heavy chain comprising the amino acid sequence of SEQ ID NO:2, or a variant thereof. In other embodiments, the anti-C5a antibody or an antigen binding fragment thereof comprises at least one of CDR1, CDR2, and CDR3 of the light chain comprising the amino acid sequence of SEQ ID NO:7, or a variant thereof.

In some embodiments, the antibodies are chimeric antibodies. In some embodiments, the anti-human C5a antibody may comprise human light chain and human heavy chain constant regions in combination with the variable region CDR sequences, or a variant thereof, described elsewhere in the specification. One of skill in the art would be able to prepare and obtain a chimeric antibody using known techniques of swapping relevant domains of specific antibodies of interest. Such an antibody is easily prepared by grafting heterogeneous antibody domains, incorporating one or more CDR sequences described in this application. Using known recombinant technology, it is possible to obtain and prepare a recombinant antibody comprising heavy and light chain constant regions encoded by nucleic acid sequences of human heavy and light chain constant regions; and the heavy and light chain variable regions comprising CDRs encoded by nucleic acid sequences corresponding to the CDR sequences set forth in the disclosure. One of skill in the art can prepare an anti-human C5a antibody comprises one or more CDR sequences described in this disclosure, wherein portions of the light chain alone or portions of the heavy chain alone are replaced with regions from an antibody belonging to another species, such as a human. A human anti-human-C5a antibody comprising variable regions having one or more CDR sequences selected from SEQ ID NOs: 3-5 and 8-10, or a variant or variants thereof, in combination with murine or non-murine antibody structural elements outside the CDR regions can be prepared by routine methods known in the art. In some embodiments, the antibodies or antibody fragments are further humanized using known techniques in the art.

In some embodiments, the anti-C5a antibody comprises an antibody having at least about 85% amino acid identity with one or more of the CDR sequences described herein, listed in SEQ ID NOs 3-5 and 8-10.

In one embodiment, the invention encompasses an anti-C5a antibody having CDR sequences of at least about 85% identity to the CDR sequences described herein. The invention encompasses an anti-C5a antibody, or antigen binding fragment thereof, having CDR sequences of that are at least about 85%, 86%, 87%, 88%, 89%, 90%, 91%, 92%, 93%, 94%, 95%, 96%, 97% 99%, or 100% identical to the CDR sequences described herein. In one embodiment, the antibody against human C5a has a heavy chain variable (vH) region and a light chain variable (vL) region, wherein the vH region has an amino acid sequence that is at least about 85% identical to SEQ ID NO: 2 and wherein the vL region has an amino acid sequence that is at least about 90% identical to SEQ ID NO: 7. In some embodiments the antibody or the antibody fragment is modified. In some embodiments, the modifications include fusion of the antibody or the antigen-binding fragment thereof with portions of another protein, or a protein fragment. In some embodiments, the antibody or the antibody fragment thereof of the invention is modified to increase the circulating half-life of the same in vivo. For example, the antibody of the fragment may be fused with an FcRn molecule, which is also known as neonatal Fc receptor to stabilize the antibody in vivo. (Nature Reviews Immunology 7:715-725). One of skill in the art would be able to prepare human C5a binding single chain variable fragment (scFv), comprising at least one CDR sequence selected from SEQ ID NOs: 3-5 and 8-10. An scFv may comprise at least one heavy chain variable region sequences designated in SEQ ID NOs: 3-5, and at least one light chain variable regions designated in SEQ ID NOs: 8-10. CDR sequences incorporated within the scFv having amino acid sequence identity of 80%, 81%, 82%, 83%, 84%, 85% 86%, 87%, 88%, 89%, 90%, 91%, 92%, 93%, 94%, 95%, 96%, 97%, 98%, 99%, or 100% to the CDR sequences described in the present disclosure are encompassed within the scope of the present disclosure.

In some embodiments the antibody or the antibody fragment is modified. In some embodiments the modifications include fusion of the antibody or the antigen-binding fragment thereof with portions of another protein, or a protein fragment. In some embodiments the antibody or the antibody fragment thereof of the invention is modified to increase the circulating half-life of the same in vivo. For example, the antibody of the fragment may be fused with an FcRn molecule, which is also known as neonatal Fc receptor to stabilize the antibody in vivo. (Nature Reviews Immunology 7:715-725). In some embodiments, the antibody or antigen-binding fragment thereof is conjugated (e.g., fused) to an effector molecule and/or another targeting moiety (such as an antibody or antibody fragment recognizing a different molecule, different antigen or a different epitope).

In various embodiments, any of the antibodies of the invention described herein, having any of the variable regions described herein, may comprise a human IgG4 constant heavy chain. In some embodiments, the antibody of the invention comprises a human IgG4 constant heavy chain having an S228P mutation.

One of skill in the art would be able to prepare C5a binding single chain variable fragment (scFv), comprising at least one specific CDR sequence selected from SEQ ID NOs 3-5, 8-10, or a variant or variants thereof Δn scFv may comprise heavy chain variable region sequences designated in SEQ ID NOs 3-5, or a variant or variants thereof, and light chain variable regions designated in SEQ ID NOs 8-10, or a variant or variants thereof. CDR sequences incorporated within the scFv having amino acid sequence identity of at least about 85% 86%, 87%, 88%, 89%, 90%, 91%, 92%, 93%, 94%, 95%, 96%, 97%, 98%, 99%, or 100% to the CDR sequences described in the present disclosure are encompassed within the scope of the present disclosure.

Screening Assays

The present invention has application in various screening assays, including, determining whether a candidate anti-C5a antibody can inhibit complement activity.

In some embodiments, the level of complement activity in the presence of the candidate anti-C5a antibody is compared with complement activity detected in a positive comparator control. The positive comparator control comprises complement activation in the absence of added test compound or in the presence of another test compound that does not bind C5a. In some embodiments, the candidate anti-C5a antibody is identified as an inhibitor of the complement when the complement activity in the presence of the candidate anti-C5a antibody is less than about 70% of the complement activity detected in a positive comparator control; this corresponds to greater than about 30% inhibition of complement activity in the presence of the test compound. In other embodiments, the candidate anti-C5a antibody is identified as an inhibitor of the complement when the complement activity in the presence of the candidate anti-C5a antibody is less than about 80% of the complement activity detected in a positive comparator control; this corresponds to greater than about 20% inhibition of complement activity in the presence of the test compound. In still other embodiments, the candidate anti-C5a antibody is identified as an inhibitor of the complement when the complement activity in the presence of the candidate anti-C5 antibody is less than about 90% of the complement activity detected in a positive comparator control; this corresponds to greater than about 10% inhibition of complement activity in the presence of the test compound. In some embodiments, the level of complement inhibition by the candidate anti-C5a antibody is compared with the level of inhibition detected in a negative comparator control.

A variety of immunoassay formats, including competitive and non-competitive immunoassay formats, antigen capture assays, two-antibody sandwich assays, and three-antibody sandwich assays are useful methods of the invention (Self et al., 1996, Curr. Opin. Biotechnol. 7:60-65). The invention should not be construed to be limited to any one type of known or heretofor unknown assay, provided that the assay is able to detect the inhibition of complement.

Enzyme-linked immunosorbent assays (ELISAs) are useful in the methods of the invention. An enzyme such as, but not limited to, horseradish peroxidase (HRP), alkaline phosphatase, beta-galactosidase or urease can be linked, for example, to an antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Chemiluminescent detection is also useful for detecting the inhibition of the complement. Chemiluminescent secondary antibodies may be obtained from any number of commercial sources.

Fluorescent detection is also useful for detecting the inhibition of the complement. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antibodies.

Radioimmunoassays (RIAs) are also useful in the methods of the invention. Such assays are well known in the art, and are described for example in Brophy et al. (1990, Biochem. Biophys. Res. Comm. 167:898-903) and Guechot et al. (1996, Clin. Chem. 42:558-563). Radioimmunoassays are performed, for example, using Iodine-125-labeled primary or secondary antibody (Harlow et al., supra, 1999).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis is performed using a spectrophotometer. It is understood that the assays of the invention can be performed manually or, if desired, can be automated and that the signal emitted from multiple samples can be detected simultaneously in many systems available commercially.

The methods of the invention also encompass the use of capillary electrophoresis based immunoassays (CEIA), which can be automated, if desired. Immunoassays also may be used in conjunction with laser-induced fluorescence as described, for example, in Schmalzing et al. (1997, Electrophoresis 18:2184-2193) and Bao (1997, J. Chromatogr. B. Biomed. Sci. 699:463-480). Liposome immunoassays, such as flow-injection liposome immunoassays and liposome immunosensors, may also be used according to the methods of the invention (Rongen et al., 1997, J. Immunol. Methods 204:105-133).

Quantitative western blotting may also be used to determine the level of complement inhibition in the methods of the invention. Western blots are quantified using well known methods such as scanning densitometry (Parra et al., 1998, J. Vasc. Surg. 28:669-675).

Methods of Administration

The methods of the invention comprise administering a therapeutically effective amount of at least one anti-C5a antibody, or binding fragment thereof (such as any of the antibodies or fragments thereof described elsewhere herein), to an individual identified as or suspected of having a complement-mediated disease or disorder. In one embodiment, the individual is a mammal having a complement system. In one embodiment, the individual a human. In various embodiments, at least one anti-C5a antibody, or binding fragment thereof, is administered locally, regionally, or systemically.

In various embodiments, the disease or disorder is at least selected from the group consisting of: macular degeneration (MD), age-related macular degeneration (AMD), ischemia reperfusion injury, arthritis, rheumatoid arthritis, asthma, allergic asthma, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, myasthenia gravis, neuromyelitis optica, (NMO), multiple sclerosis, delayed graft function, antibody-mediated rejection, atypical hemolytic uremic (aHUS) syndrome, central retinal vein occlusion (CRVO), central retinal artery occlusion (CRAO), epidermolysis bullosa, sepsis, septic shock, organ transplantation, inflammation (including, but not limited to, inflammation associated with cardiopulmonary bypass surgery and kidney dialysis), C3 glomerulopathy, membranous nephropathy, IgA nephropathy, glomerulonephritis (including, but not limited to, anti-neutrophil cytoplasmic antibody (ANCA)-mediated glomerulonephritis, lupus nephritis, and combinations thereof), ANCA-mediated vasculitis, Shiga toxin induced HUS, and antiphospholipid antibody-induced pregnancy loss, or any combinations thereof. In some embodiments, the AP-mediated disease is sepsis, septic shock, rheumatoid arthritis, autoimmune hemolytic anemia, GvHD, anti-phospholipid syndrome, or Gaucher's disease. The methods of the invention can comprise the administration of at least one anti-C5a antibody, or binding fragment thereof, but the present invention should in no way be construed to be limited to the anti-C5a antibodies described herein, but rather should be construed to encompass any anti-C5a antibody, both known and unknown, that diminish and reduce complement activation.

The method of the invention comprises administering a therapeutically effective amount of at least one anti-C5a antibody, or binding fragment thereof, to an individual wherein a composition of the present invention comprising at least one anti-C5a antibody, or binding fragment thereof, either alone or in combination with at least one other therapeutic agent. The invention can be used in combination with other treatment modalities, such as, for example anti-inflammatory therapies, and the like. Examples of anti-inflammatory therapies that can be used in combination with the methods of the invention include, for example, therapies that employ steroidal drugs, as well as therapies that employ non-steroidal drugs.

The method of the invention comprises administering a therapeutically effective amount of an anti-C5a antibody, or an antigen-binding fragment thereof, to a subject. In some embodiments, the invention encompasses a method of treatment of C5a related diseases involving dysregulation of the complement signaling by administering a therapeutically effective amount of an antibody of the invention, or a therapeutically effective amount of an antibody fragment thereof, such that a reduction of C5a activity is effected in the subject. In some embodiments, the invention encompasses a method of treatment of C5a related diseases involving dysregulation of complement signaling by administering a therapeutically effective amount of an antibody or an antibody fragment. In some embodiments, the invention encompasses a method of treatment of C5a related diseases involving dysregulation of complement signaling by administering to a subject an effective amount of an antibody, an antibody fragment, a polypeptide, a peptide, or a conjugated peptide, such that the complement activity is reduced in the subject. In some embodiments, the method of treatment encompasses administering to a subject a systemically effective dose of an antibody or an antibody fragment, whereby systemic reduction of C5a activity is effected in the subject.

Administration of an anti-C5a antibody, or binding fragment thereof, in a method of treatment of the invention can be achieved in a number of different ways, using methods known in the art. The therapeutic and prophylactic methods of the invention thus encompass the use of pharmaceutical compositions comprising an anti-C5a antibody.

The pharmaceutical compositions useful for practicing the invention may be administered to deliver a dose of at least about 1 ng/kg, at least about 5 ng/kg, at least about 10 ng/kg, at least about 25 ng/kg, at least about 50 ng/kg, at least about 100 ng/kg, at least about 500 ng/kg, at least about 1 μg/kg, at least about 5 μg/kg, at least about 10 μg/kg, at least about 25 μg/kg, at least about 50 μg/kg, at least about 100 μg/kg, at least about 500 μg/kg, at least about 1 mg/kg, at least about 5 mg/kg, at least about 10 mg/kg, at least about 25 mg/kg, at least about 50 mg/kg, at least about 100 mg/kg, at least about 200 mg/kg, at least about 300 mg/kg, at least about 400 mg/kg, and at least about 500 mg/kg of body weight of the subject. In one embodiment, the invention administers a dose which results in a concentration of the C5a antibody, or binding fragment thereof, of the present invention of at least about 1 pM, at least about 10 pM, at least about 100 pM, at least about 1 nM, at least about 10 nM, at least about 100 nM, at least about 1 μM, at least about 2 μM, at least about 3 μM, at least about 4 μM, at least about 5 μM, at least about 6 μM, at least about 7 μM, at least about 8 μM, at least about 9 μM and at least about 10 μM in an individual. In another embodiment, the invention envisions administration of a dose which results in a concentration of the C5a antibody, or binding fragment thereof, of the present invention between at least about 1 pM, at least about 10 pM, at least about 100 pM, at least about 1 nM, at least about 10 nM, at least about 100 nM, at least about 1 μM, at least about 2 μM, at least about 3 μM, at least about 4 μM, at least about 5 μM, at least about 6 μM, at least about 7 μM, at least about 8 μM, at least about 9 μM and at least about 10 μM in the plasma of an individual.

In some embodiments, the pharmaceutical compositions useful for practicing the invention may be administered to deliver a dose of no more than about 1 ng/kg, no more than about 5 ng/kg, no more than about 10 ng/kg, no more than about 25 ng/kg, no more than about 50 ng/kg, no more than about 100 ng/kg, no more than about 500 ng/kg, no more than about 1 μg/kg, no more than about 5 μg/kg, no more than about 10 μg/kg, no more than about 25 μg/kg, no more than about 50 μg/kg, no more than about 100 μg/kg, no more than about 500 μg/kg, no more than about 1 mg/kg, no more than about 5 mg/kg, no more than about 10 mg/kg, no more than about 25 mg/kg, no more than about 50 mg/kg, no more than about 100 mg/kg, no more than about 200 mg/kg, no more than about 300 mg/kg, no more than about 400 mg/kg, and no more than about 500 mg/kg of body weight of the subject. In one embodiment, the invention administers a dose which results in a concentration of the anti-C5a antibody of the present invention of no more than about 1 pM, no more than about 10 pM, no more than about 100 pM, no more than about 1 nM, no more than about 10 nM, no more than about 100 nM, no more than about 1 μM, no more than about 2 μM, no more than about 3 μM, no more than about 4 μM, no more than about 5 μM, no more than about 6 μM, no more than about 7 μM, no more than about 8 μM, no more than about 9 μM and no more than about 10 μM in an individual. In another embodiment, the invention envisions administration of a dose which results in a concentration of the anti-C5a antibody of the present invention between no more than about 1 pM, no more than about 10 pM, no more than about 100 pM, no more than about 1 nM, no more than about 10 nM, no more than about 100 nM, no more than about 1 μM, no more than about 2 μM, no more than about 3 μM, no more than about 4 μM, no more than about 5 μM, no more than about 6 μM, no more than about 7 μM, no more than about 8 μM, no more than about 9 μM and no more than about 10 μM in the plasma of an individual. Also contemplated are dosage ranges between any of the doses disclosed herein.

Typically, dosages which may be administered in a method of the invention to a subject, in some embodiments a human, range in amount from 0.5 μg to about 50 mg per kilogram of body weight of the subject. While the precise dosage administered will vary depending upon any number of factors, including but not limited to, the type of subject and type of disease state being treated, the age of the subject and the route of administration. In some embodiments, the dosage of the compound will vary from about 1 μg to about 10 mg per kilogram of body weight of the subject. In other embodiments, the dosage will vary from about 3 μg to about 1 mg per kilogram of body weight of the subject.

The antibody may be administered to a subject as frequently as several times daily, or it may be administered less frequently, such as once a day, twice a day, thrice a day, once a week, twice a week, thrice a week, once every two weeks, twice every two weeks, thrice every two weeks, once a month, twice a month, thrice a month, or even less frequently, such as once every several months or even once or a few times a year or less. The frequency of the dose will be readily apparent to the skilled artisan and will depend upon any number of factors, such as, but not limited to, the type and severity of the disease being treated, the type and age of the subject, etc. The formulations of the pharmaceutical compositions may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various subjects is well understood, and the ordinarily skilled veterinary pharmacologist can design and perform such modification with merely ordinary, if any, experimentation. Individuals to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intraocular, intravitreal, intramuscular, intradermal and intravenous routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to an individual or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the individual treated and further depending upon the route by which the composition is to be administered. By way of example, the composition may comprise between 0.1% and 100% (w/w) active ingredient. In various embodiments, the composition comprises at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Parenteral administration of a pharmaceutical composition includes any route of administration characterized by physical breaching of a tissue of an individual and administration of the pharmaceutical composition through the breach in the tissue. Parental administration can be local, regional or systemic. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraocular, intravitreol, intravitreal, subcutaneous, intraperitoneal, intramuscular, intradermal, intrasternal injection, and intratumoral.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and in some embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In some embodiments, such powders comprise particles wherein at least 98% of the particles by weight have a diameter greater than 0.5 nanometers and at least 95% of the particles by number have a diameter less than 7 nanometers. In some embodiments, at least 95% of the particles by weight have a diameter greater than 1 nanometer and at least 90% of the particles by number have a diameter less than 6 nanometers. In some embodiments, dry powder compositions include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. In some embodiments, the droplets provided by this route of administration have an average diameter in the range from about 0.1 to about 200 nanometers.

The formulations are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more additional ingredients.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more additional ingredients. Alternately, formulations suitable for buccal administration may comprise a powder or an aerosolized or atomized solution or suspension comprising the active ingredient. In some embodiments, such powdered, aerosolized, or aerosolized formulations, when dispersed, have an average particle or droplet size in the range from about 0.1 to about 200 nanometers, and may further comprise one or more additional ingredients.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Cells Producing Antibodies and Antigen Binding Fragments Thereof

In some embodiments, the invention is a cell or cell line (such as host cells) that produces at least one of the anti-C5a antibodies, or antigen binding fragments, described herein. In one embodiment, the cell or cell line is a genetically modified cell that produces at least one of the anti-C5a antibodies, or antigen binding fragments, described herein. In one embodiment, the cell or cell line is a hybridoma that produces at least one of the anti-C5a antibodies, or antigen binding fragments, described herein.

Hybrid cells (hybridomas) are generally produced from mass fusions between murine splenocytes, which are highly enriched for B-lymphocytes, and myeloma "fusion partner cells" (Alberts et al., Molecular Biology of the Cell (Garland Publishing, Inc. 1994); Harlow et al., Antibodies. A Laboratory Manual (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are referred to as monoclonal antibodies.

Also provided are nucleic acids encoding any of the antibodies, or antibody fragments, disclosed herein, as well as vectors comprising the nucleic acids. Thus, the antibodies and fragments of the invention can be generated by expressing the nucleic acid in a cell or a cell line, such as the cell lines typically used for expression of recombinant or humanized immunoglobulins. Thus, the antibodies and fragments of the invention can also be generated by cloning the nucleic acids into one or more expression vectors, and transforming the vector into a cell line such as the cell lines typically used for expression of recombinant or humanized immunoglobulins.

The genes encoding the heavy and light chains of immunoglobulins, or fragments thereof, can be engineered according to methods, including but not limited to, the polymerase chain reaction (PCR), known in the art (see, e.g., Sambrook et al., Molecular Cloning: A Laboratory Manual, 2nd ed., Cold Spring Harbor, N.Y., 1989; Berger & Kimmel, Methods in Enzymology, Vol. 152: Guide to Molecular Cloning Techniques, Academic Press, Inc., San Diego, Calif., 1987; Co et al., 1992, J. Immunol. 148:1149). For example, genes encoding heavy and light chains, or fragments thereof, can be cloned from an antibody secreting cell's genomic DNA, or cDNA is produced by reverse transcription of the cell's RNA. Cloning is accomplished by conventional techniques including the use of PCR primers that hybridize to the sequences flanking or overlapping the genes, or segments of genes, to be cloned.

Nucleic acids encoding the antibody of the invention, or the heavy chain or light chain or fragments thereof, can be obtained and used in accordance with recombinant nucleic acid techniques for the production of the specific immunoglobulin, immunoglobulin chain, or a fragment or variant thereof, in a variety of host cells or in an in vitro translation system. For example, the antibody-encoding nucleic acids, or fragments thereof, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

In some embodiments, the heavy and light chains, or fragments thereof, can be assembled in two different expression vectors that can be used to co-transfect a recipient cell. In some embodiments, each vector can contain two or more selectable genes, one for selection in a bacterial system and one for selection in a eukaryotic system. These vectors allow for the production and amplification of the genes in a bacterial system, and subsequent co-transfection of eukaryotic cells and selection of the co-transfected cells. The selection procedure can be used to select for the expression of antibody nucleic acids introduced on two different DNA vectors into a eukaryotic cell.

Alternatively, the nucleic acids encoding the heavy and light chains, or fragments thereof, may be expressed from one vector. Although the light and heavy chains are coded for by separate genes, they can be joined, using recombinant methods. For example, the two polypeptides can be joined by a synthetic linker that enables them to be made as a single protein chain in which the $V_L$ and $V_H$ regions pair to form monovalent molecules (known as single chain Fv (scFv); see e.g., Bird et al., 1988, Science 242: 423-426; and Huston et al., 1988, Proc. Natl. Acad. Sci. USA 85:5879-5883).

The invention provides for an isolated nucleic acid molecule comprising a nucleic acid sequence encoding a heavy chain and/or a light chain, as well as fragments thereof. A nucleic acid molecule comprising sequences encoding both the light and heavy chain, or fragments thereof, can be engineered to contain a synthetic signal sequence for secretion of the antibody, or fragment, when produced in a cell. Furthermore, the nucleic acid molecule can contain specific DNA links which allow for the insertion of other antibody sequences and maintain the translational reading frame so to not alter the amino acids normally found in antibody sequences.

In accordance with the present invention, antibody-encoding nucleic acid sequences can be inserted into an appropriate expression vector. In various embodiments, the expression vector comprises the necessary elements for transcription and translation of the inserted antibody-encoding nucleic acid so as to generate recombinant DNA molecules that direct the expression of antibody sequences for the formation of an antibody, or a fragment thereof.

The antibody-encoding nucleic acids, or fragments thereof, can be subjected to various recombinant nucleic acid techniques known to those skilled in the art such as site-directed mutagenesis.

A variety of methods can be used to express nucleic acids in a cell. Nucleic acids can be cloned into a number of types of vectors. However, the present invention should not be construed to be limited to any particular vector. Instead, the present invention should be construed to encompass a wide variety of vectors which are readily available and/or known in the art. For example, the nucleic acid of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Viral vector technology is well known in the art and is described, for example, in Sambrook et al. (2012), and in Ausubel et al. (1999), and in other virology and molecular biology manuals. Viruses, which are useful as vectors include, but are not limited to, retroviruses, adenoviruses, adeno-associated viruses, herpes viruses, and lentiviruses. In some embodiments, a murine stem cell virus (MSCV) vector is used to express a desired nucleic acid. MSCV vectors have been demonstrated to efficiently express desired nucleic acids in cells. However, the invention should not be limited to only using a MSCV vector, rather any retroviral expression method is included in the invention. Other examples of viral vectors are those based upon Moloney Murine Leukemia Virus (MoMuLV) and HIV. In some embodiments, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193).

Additional regulatory elements, e.g., enhancers, can be used modulate the frequency of transcriptional initiation. A promoter may be one naturally associated with a gene or nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high-level expression of the introduced DNA segment, such as is advantageous in the large-scale production of recombinant proteins and fragments thereof.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue-specific promoter or cell-type specific promoter, which is a promoter that is active only in a desired tissue or cell. Tissue-specific promoters are well known in the art and include, but are not limited to, the HER-2 promoter and the PSA associated promoter sequences.

In order to assess the expression of the nucleic acids, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate nucleic acid and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing nucleic acids into a cell are known in the art. In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, laserporation and the like. Methods for producing cells comprising vectors and/or exogenous nucleic acids are well-known in the art. See, for example, Sambrook et al. (2012) and Ausubel et al. (1999).

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (e.g., an artificial membrane vesicle). The preparation and use of such systems is well known in the art.

Regardless of the method used to introduce exogenous nucleic acids into a host cell or otherwise expose a cell to the nucleic acid of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Kits

The invention also includes a kit comprising an anti-C5a antibody, or combinations thereof, of the invention and an instructional material which describes, for instance, administering the anti-C5a antibody, or combinations thereof, to an individual as a therapeutic treatment or a non-treatment use as described elsewhere herein. In an embodiment, this kit further comprises a (optionally sterile) pharmaceutically acceptable carrier suitable for dissolving or suspending the therapeutic composition, comprising an anti-C5a antibody, or combinations thereof, of the invention, for instance, prior to administering the antibody to an individual. Optionally, the kit comprises an applicator for administering the antibody.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore and are not to be construed as limiting in any way the remainder of the disclosure.

Example 1

The complement system is part of innate immunity that plays a key role in host defense. However, activated complement also has the potential to cause significant tissue injury and destruction and dysregulated complement activity has been found to be associated with a number of rare and common diseases such as paroxysmal nocturnal hemoglobinuria (PNH), atypical hemolytic uremic syndrome, rheumatoid arthritis, sepsis, age-related macular degeneration etc. Thus, anti-complement therapy is a promising way of treating these human disorders. Complement C5 is a critical protein in the terminal pathway of complement activation and is the precursor protein for generating the potent proinflammatory mediator C5a, as well as the cytolytic membrane attack complex (MAC), C5b-9.

A function-blocking anti-human C5a monoclonal antibody (7A12) was developed and is described herein. This mAb blocks C5a-mediated activity but does not block MAC activity (assessed in a hemolytic assay).

The methods and material used in this example are now described.

Western-Blotting

Purified human C5 protein (1 μg) was boiled in sample buffer and loaded onto 6% SDS-PAGE gels under non-reducing or reducing conditions. The proteins were blotted onto PVDF membranes, which were probed with 10 μg/ml of primary antibody (mAb 7A12 or control anti-C5 mAb) for 1 hour, followed by detection with HRP anti-mouse IgG (1:4000, Bio-Rad).

Human C5, C5a and mAb Binding Assay

Polystyrene microtiter plates were coated with purified human C5 or C5a (50 ng/well, Hycult) in PBS at 37° C. for 1 hr. After aspirating the C5 or C5a solution, wells were blocked with PBS containing 1% BSA in PBS at room temperature for 1 hour. Wells without C5 or C5a coating served as background controls. Different concentration of 7A12 mAb or control anti-C5 mAb or chimeric 7A12, 50 μl/well in blocking solution, were added to the wells. Following 1 hour incubation at room temperature, the wells were extensively washed with PBST. Human C5 or C5a-bound mAb was detected by the addition of anti-mouse IgG HRP 1:4000 dilution in blocking solution, which was allowed to incubate for 1 hour at RT. After washing with PBST, the plate was developed with HRP substrate for 6-10 min. The reaction was stopped with 2N H2SO4 and plate was read at 450 nm in a micro plate reader.

Mouse C5a and mAb Binding Assay

Polystyrene microtiter plates were coated with purified mouse C5a (50 ng/well, Hycult) in PBS at 37° C. for 1 hour. After aspirating the C5a solution, wells were blocked with PBS containing 1% BSA in PBS at room temperature for 1 hour. Wells without C5a coating served as background controls. Different concentration of 7A12 mAb or control anti-C5 mAb or chimeric 7A12, 50 μl/well in blocking solution, were added to the wells. Following 1 hour incubation at room temperature, the wells were extensively washed with PBST. Mouse C5a-bound mAb was detected by the addition of anti-mouse IgG HRP 1:4000 dilution in blocking solution, which incubated for 1 hour at room temperature (RT). After washing with PBST, the plate was developed with HRP substrate for 6-10 minutes. The reaction was stopped with 2 N $H_2SO_4$ and plate was read at 450 nm in a micro plate reader.

Generation of Anti-Human C5a mAbs:

B10.D2/oSnJ female (Stock #000461, Jackson laboratory) mice were immunized with 30 μg of purified human C5 (#A120, Complement Technology, Inc) emulsified with adjuvant. At day 14, the mice were again immunized with 30 μg of purified human C5 emulsified with adjuvant. Mice were boosted with 33 μg of purified human C5 three times before fusion. Then, mice were sacrificed by cervical dislocation and spleen was isolated for preparation of single cell suspension by mechanical disruption. The spleen cell suspension was washed once with hybridoma serum-free media (HYB-SFM) (Invitrogen)+10% FBS medium and cells were counted, and mixed with X63-Ag8.653 myeloma cells (ATCC) in a 2:1 ratio. Cell mixture was again washed with HYB-SFM medium, and the cell pellet was prepared by centrifugation (1000 rpm×5 minutes). The cell pellet was gently disturbed and loosened and then cell fusion was induced by slowly adding poly ethylene glycol (PEG 1500) (1.5 ml PEG for $3\times10^8$ cells). The cells were left for 1 min at 37° C. and then 20 ml HYB-SFM medium were added to the cells in 3 min (1 ml for the first minute, 3 ml for the second minute and 16 ml for the third minute). The mixture was centrifuged at 1000 rpm for 5 minutes and the cells were plated in 24-well plates in HAT medium (10 ml HAT [Sigma H0262], 5 ml Pen/Strep, 500 μl Gentamicin and 10% FBS in 500 ml HYB-SFM medium). After 2 weeks, supernatants from wells with visible colonies were withdrawn for screening of reactivity with purified human C5 by ELISA. Positive clones were picked up and plated in 96-well plates by limiting dilution method to obtain single clones after second round screening by ELISA. Positive clones were expanded in HT-medium (10 ml HT, 5 ml Pen/Strep 500 μl Gentamicin and 10% FBS in 500 ml HYB-SFM medium). Before antibody collection, the hybridoma cells were switched to serum-free medium (HYB-SFM) for 2-3 days. Cell culture medium was collected for mAb purification by protein G affinity chromatography.

mAb Cloning:

To clone the cDNAs of 7A12, total RNAs were isolated from the hybridoma cells by TRizol reagent (Sigma). First-strand cDNAs were synthesized by reverse transcription using Oligo(dT) primer, To amplify the heavy chain cDNAs (for IgG1, IgG2a/b), the following primers were used in PCR reactions: 5'-GAG GTG A AGCTG GTG G AG(T/A) C(T/A) GG-3' (SEQ ID NO:11) and 5'-GGGGCCAGTG-GATAGAC-3' (SEQ ID NO:12). To amplify the k light chain, the following primers were used: mixture of 4 upstream primers: 5 CCAGTTCCGAGCTCCA-GATGACCCAGACTCCA-3' (SEQ ID NO: 70); 5'-CCAGTTCCGAGCTCGTGCTCACCCAGTCTCCA-3' (SEQ ID NO:71); 5'-CCAGTTCCGAGCTCCA-GATGACCCAGTCTCCA-3' (SEQ ID NO:72); 5'-CC AGTTC CG A G CTC GTG ATG AC AC AGTCTCC A-3' (SEQ ID NO:13); downstream primer: 5'-GTTGGTGCAG-CATCAGC-3, (SEQ ID NO:14). The PCR amplicons were cloned into pCR TOPO TA 2.1 vector (Invitrogen) and sequenced. To obtain the signal peptide (leader) sequence of the mAbs, the 5'-RACE method was used with a kit (GeneRacer) from Invitrogen. The complete variable region cDNAs were amplified using specific primers determined from the 5'-RACE and the initial sequencing data.

Hemolysis Assay

Antibody-sensitized sheep RBCs ($1\times10^7$ cells, Complement Technology, Inc.) were incubated at 37° C. for 20 minutes with 50% NHS (Complement Technology, Inc) in gelatin veronal buffer (GVB2+, Sigma). Before addition to the sheep RBCs, NHS was pre-incubated with 7A12 mAb or control anti-C5 mAb for 1 hour at 4° C. Lysis reaction was stopped by addition of ice-cold 40 mM EDTA in PBS. The incubation mixtures were centrifuged for 5 minutes at 1500 rpm and the supernatant was collected and measured for OD405 nm. Samples without NHS or with EDTA added were used as negative lysis controls, and a sample of sheep RBCs lysed completely with distilled water was used as a positive control (100% lysis) against which % lysis in other samples was normalized.

Transwell Migration Assay

U937 cells stably transfected with the C5a receptor (U937-C5aR cells), these were seeded ($1\times10^6$ cells per well, in the chemotaxis assay buffer) onto the upper chambers of 24-well Transwell inserts with 3.0-μm pore size polycarbonate membrane filter (Corning). The lower Boyden chambers received 10 nM of recombinant human complement C5a pretreated with antibody (1 μg/ml or 10 μg/ml) in the chemotaxis assay buffer. After a 3-hour incubation at 37° C., the migrated cells in the lower chambers were collected and counted using Coulter counter (Beckman Coulter). (Chemotaxis assay buffer: RPMI 1640 medium with 0.5% BSA).

Calcium Mobilization Assay $1\times10^7$ of cells were washed twice with HEPES buffer for calcium mobilization assay (25 mM HEPES, 119 mM NaCl, 5 mM KCl, 5.6 mM glucose, 0.4 mM $MgCl_2$, and 1 mM $CaCl_2$)) containing 1 mg/ml BSA, and afterward incubated with 1 μM indo-1 acetoxymethyl ester (Anaspec, Inc, Fremont, Calif., USA) at room temperature for 30 minutes. Subsequently, cells were washed twice and resuspended in 1.3 mL of the same buffer. Human C5a and antibody were mixed so as to be 10 nM and 50 μg/ml respectively in the final concentration for 10 minutes at room temperature. Finally, intercellular $Ca^{2+}$ measurements were performed using Infinite F200 multimode microplate reader (Tecan Systems Inc, San Jose, Calif., USA) with an excitation wavelength of 360 nm and an emission wavelength of 415 nm. Addition of the mixture was performed at 300 seconds after the starting measurement.

The results of this example are now described.

As depicted in FIG. 1, 7A12 was shown to bind to human C5. The reactivity of 7A12 and 2G1, a control anti-C5 mAb, with intact human C5 was assessed by ELISA, shown in FIG. 1. An ELISA plate was coated with purified human C5. After incubation with serially diluted 7A12 or control anti-C5 mAb, bound mAb was detected by HRP-conjugated rabbit anti-mouse IgG. Both 7A12 and the control anti-C5 mAb showed high reactivity with human C5. By western-blotting, mAb 7A12 and the control anti-C5 mAb recognized purified human C5 protein under non-reducing and reducing conditions, respectively, shown in FIG. 1B. The observed 7A12-reactive 190 kDa band represents the whole C5 protein, whereas the 115 kDa band represents the C5 α-chain.

Figure 2:
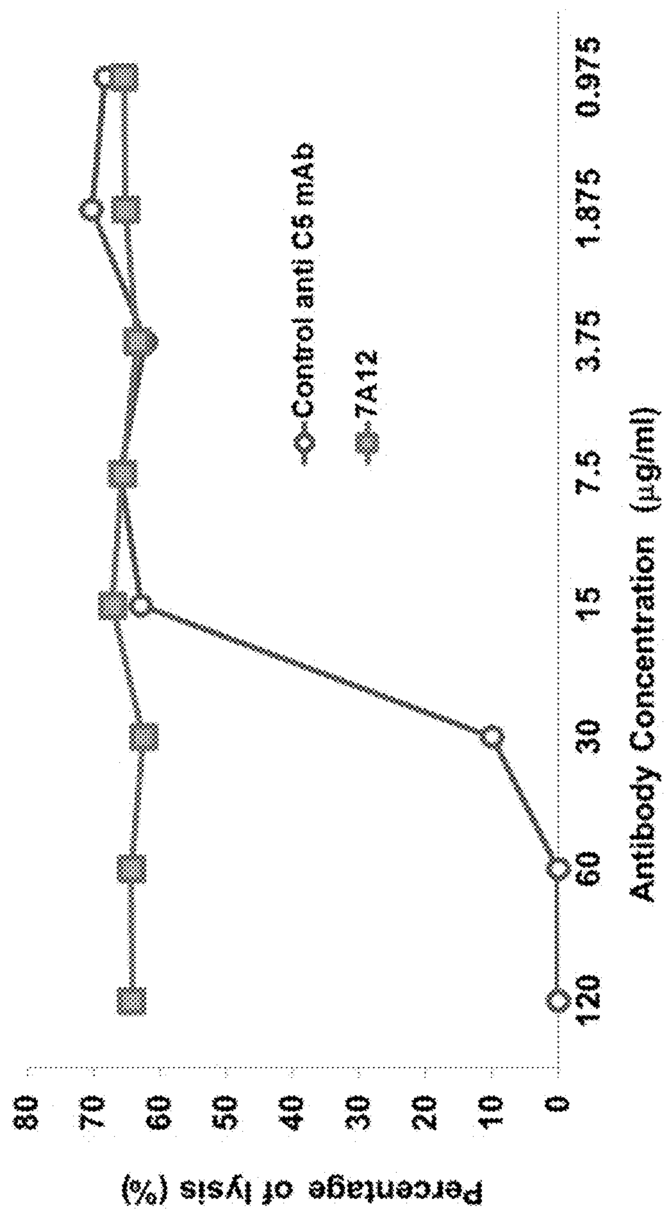
FIG. 2 depicts results showing that, unlike the control C5 mAb 2G1 which inhibits red blood cell (RBC) lysis, 7A12 has no activity in a hemolysis assay. Antibody-sensitized sheep RBCs were incubated with normal human serum (NHS) containing serial dilutions of 7A12 or the control anti-C5 mAb at 37° C. for 1 hour. RBC lysis was determined by measuring the absorbance at OD405 nm. As expected, the control anti-C5 mAb 2G1 inhibited 50% NHS-mediated sheep erythrocyte lysis in a dose-dependent manner. On the other hand, at doses of 0.975 to 120 μg/ml, mAb 7A12 showed no inhibition of 50% NHS-mediated sheep erythrocyte lysis.

Unlike the control C5 mAb 2G1 which inhibits red blood cell (RBC) lysis, 7A12 was demonstrated to have no activity in a hemolysis assay, depicted in FIG. 2. Antibody-sensitized sheep RBCs were incubated with normal human serum (NHS) containing serial dilutions of 7A12 or the control anti-C5 mAb at 37 C for 1 hr. RBC lysis was determined by measuring the absorbance at OD405 nm. As expected, control anti-C5 mAb inhibited 50% NHS-mediated sheep erythrocyte lysis in a dose-dependent manner. On the other hand, at doses of 0.975 to 120 μg/ml, mAb 7A12 showed no inhibition of 50% NHS-mediated sheep erythrocyte lysis.

Figure 3:
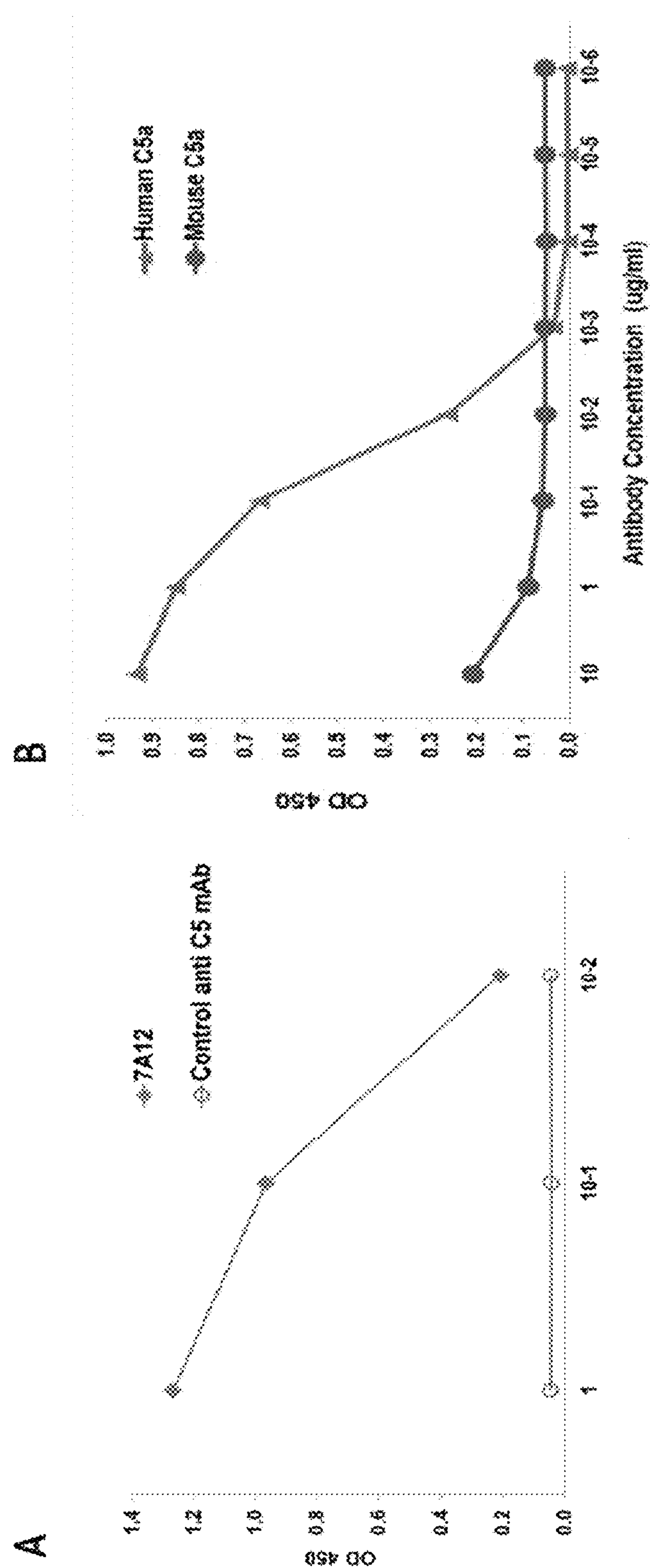
FIG. 3, comprising

Unlike the control anti-C5 mAb 2G1 that does not bind C5a, 7A12 was shown to bind to human C5a. An ELISA plate was coated with human C5a or mouse C5a. After incubation with serially diluted 7A12 or the control anti-C5 mAb, bound mAb was detected by HRP-conjugated anti-mouse IgG. FIG. 3A demonstrates that mAb 7A12 showed high reactivity to human C5a. Since mAb 7A12 reacts with the whole C5 protein (as shown in FIG. 1), it can be concluded that mAb 7A12 binds both the C5a moiety of native human C5 and free human C5a. On the other hand, no binding of the control anti-C5 mAb to human C5a was seen, as depicted in FIG. 3B. Binding of mAb 7A12 to C5a was found to be specific to human C5a with little binding to mouse C5a.

Figure 4:
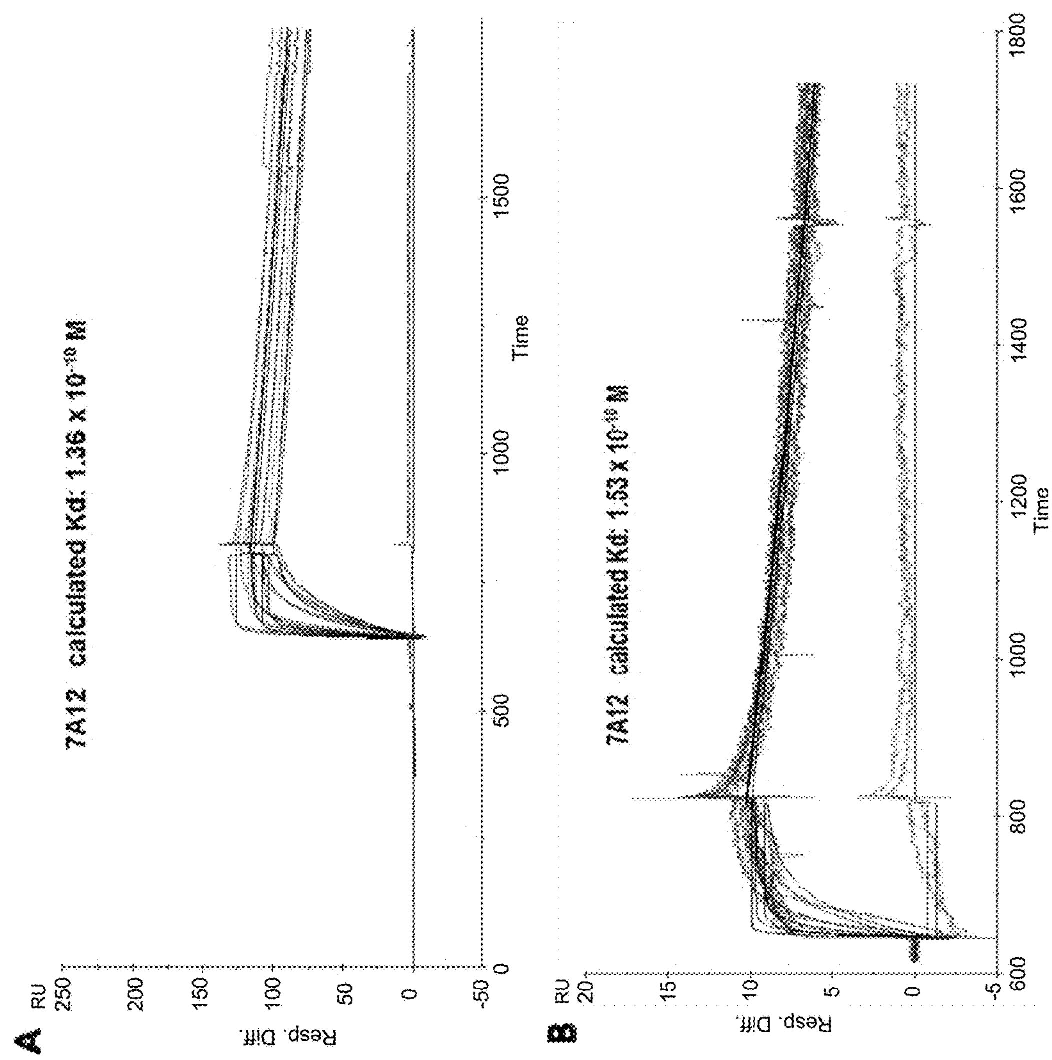
FIG. 4, comprising

Binding affinity of mAb 7A12 to human C5 and C5a. Purified human C5 or C5a was coupled onto CM4 chip using the amine coupling method. Biacore analysis was performed on a Biacore-2000 instrument. The chip was regenerated between each binding using 50 mM NaOH. mAb 7A12 binds to human C5, shown in FIG. 4A, and human C5a, shown in FIG. 4B, with similar affinities.

Figure 5:
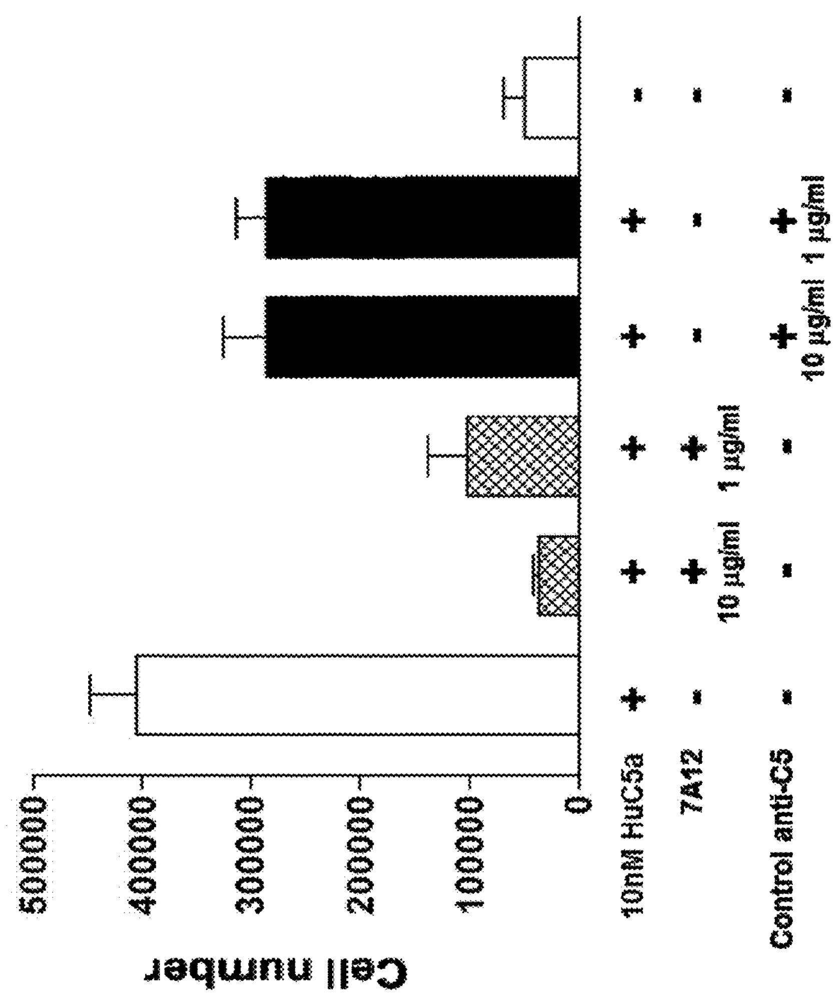
FIG. 5 depicts results demonstrating that mAb 7A12, but not the control anti-C5 mAb 2G1, inhibits C5a-mediated neutrophil migration. Human C5a at 10 nM was used to induce chemotaxis of the human monocytic cell line, U937 transfected with the human C5a receptor. Cells were placed in the upper chamber of a trans-well plated in the presence of mAb 7A12 or the control anti-C5 mAb 2G1, and cell migration was quantified by counting the cells in the lower chamber. mAb 7A12 showed complete inhibition of C5a-induced chemotaxis at 10 μg/ml whereas the control anti-C5 mAb 2G1 failed to block C5a-induced chemotaxis.

Results shown in FIG. 5 demonstrate that mAb 7A12 but not the control anti-C5 mAb 2G1 inhibits C5a-mediated neutrophil migration. Human C5a at 10 nM was used to induce chemotaxis of the human monocytic cell line, U937 transfected with the human C5a receptor. Cells were placed in the upper chamber of a trans-well plated in the presence of mAb 7A12 or the control anti-C5 mAb 2G1, and cell migration was quantified by counting the cells in lower chamber. mAb 7A12 showed complete inhibition of C5a-induced chemotaxis at 10 μg/ml whereas the control anti-C5 mAb 2G1 failed to block C5a-induced chemotaxis.

Figure 6:
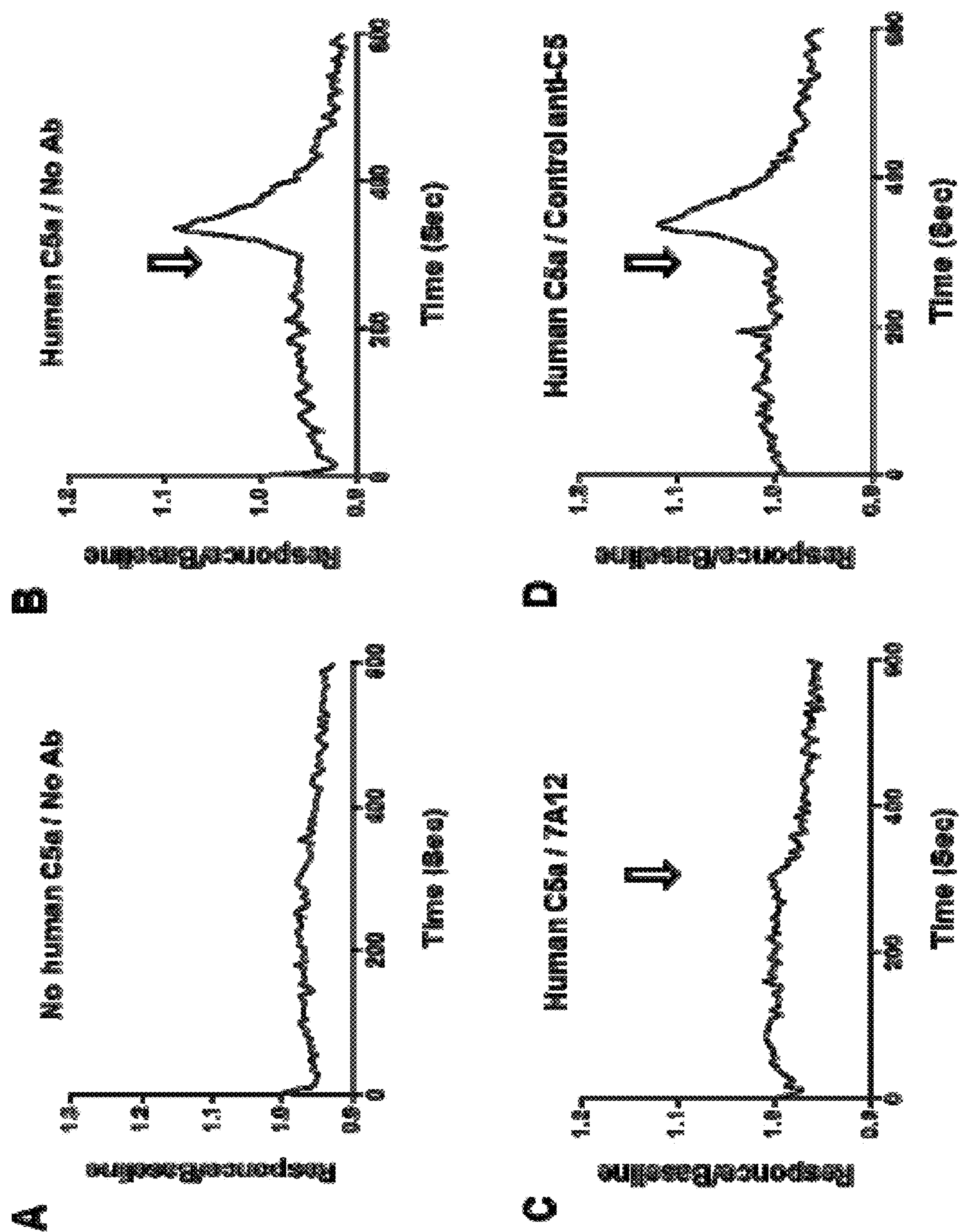
FIG. 6, comprising

Results shown in FIG. 6 demonstrate that mAb 7A12 but not the control anti-C5 mAb 2G1 inhibits C5a-induced intracellular calcium mobilization in U937 cells. No calcium mobilization occurred in U937 cells expressing the human C5a receptor (U937-C5aR) in the absence of human C5a stimulation, shown in FIG. 6A. C5a treatment led to a transient calcium influx in U937-C5aR cells, shown in FIG. 6B, which could be inhibited by pre-incubation with mAb 7A12 (50 μg/ml), shown in FIG. 6C, but not with the control anti-C5 mAb 2G1 (50 μg/ml), shown in FIG. 6D. Arrows refer to the time point when a mixture of C5a and antibody was added to the cell suspension.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An antibody that specifically binds to human C5a, wherein the antibody comprises a heavy chain variable (VH) region and a light chain variable (VL) region, wherein the VH region comprises i) a VH-CDR1 comprising the amino acid sequence of SEQ ID NO: 3;

ii) a VH-CDR2 comprising the amino acid sequence of SEQ ID NO: 4; and iii) a VH-CDR3 comprising the amino acid sequence of SEQ ID NO: 5; and wherein the VL region comprises i) a VL-CDR1 comprising the amino acid sequence of SEQ ID NO: 8;

ii) a VL-CDR2 comprising the amino acid sequence of SEQ ID NO: 9; and iii) a VL-CDR3 comprising the amino acid sequence of SEQ ID NO: 10.

2. The antibody of claim 1, wherein the antibody is a chimeric antibody.

3. The antibody of claim 1, wherein the antibody comprises a heavy chain comprising the amino acid sequence of SEQ ID NO:2, or a variant thereof.

4. The antibody of claim 1, wherein the antibody comprises a light chain comprising the amino acid sequence of SEQ ID NO:7, or a variant thereof.

5. The antibody of claim 1, wherein the antibody comprises a heavy chain comprising the amino acid sequence of SEQ ID NO:2, or a variant thereof, and a light chain comprising the amino acid sequence of SEQ ID NO:7, or a variant thereof.

6. A method of treating a complement pathway-mediated disease or disorder in an individual, comprising the step of administering to said individual the anti-C5a antibody of claim 1.

7. The method of claim 6, wherein the disease or disorder is at least one selected from the group consisting of: macular degeneration (MD), age-related macular degeneration (AMD), ischemia reperfusion injury, arthritis, rheumatoid arthritis, lupus, ulcerative colitis, stroke, post-surgery systemic inflammatory syndrome, asthma, allergic asthma, chronic obstructive pulmonary disease (COPD), paroxysmal nocturnal hemoglobinuria (PNH) syndrome, autoimmune hemolytic anemia (AIHA), Gaucher disease, myasthenia gravis, neuromyelitis optica, (NMO), multiple sclerosis, delayed graft function, antibody-mediated rejection, atypical hemolytic uremic syndrome (aHUS), central retinal vein occlusion (CRVO), central retinal artery occlusion (CRAO), epidermolysis bullosa, sepsis, septic shock, organ transplantation, inflammation, inflammation associated with cardiopulmonary bypass surgery and kidney dialysis, C3 glomerulopathy, membranous nephropathy, IgA nephropathy, glomerulonephritis, anti-neutrophil cytoplasmic antibody (ANCA)-mediated glomerulonephritis, lupus nephritis, ANCA-mediated vasculitis, Shiga toxin induced HUS, antiphospholipid antibody-induced pregnancy loss, graft versus host disease (GVHD), and any combinations thereof.

8. The antibody of claim 1, wherein the antibody has a heavy chain variable (VH) region that has an amino acid sequence that is more than 90% identical to SEQ ID NO: 2.

9. The antibody of claim 8, wherein the antibody is an antibody fragment selected from the group consisting of a Fab, Fab', F(ab)2, F(ab')2, scFv, and combinations thereof.

10. The antibody of claim 1, wherein the antibody has a light chain variable (VL) region that has an amino acid sequence that is more than 90% identical to SEQ ID NO: 7.

11. The antibody of claim 10, wherein the antibody is an antibody fragment selected from the group consisting of a Fab, Fab', F(ab)2, F(ab')2, scFv, and combinations thereof.

12. A cell comprising the antibody of claim 1.

13. The cell of claim 12, wherein the cell produces the antibody of claim 1.

14. The cell of claim 12, wherein the cell is a hybridoma.

15. A method of reducing the activity of a complement system of an individual, wherein the method comprises administering an antibody to the individual via a route of administration selected from the group consisting of enteral administration, parenteral administration, and a combination thereof, and wherein the antibody comprises six complementarity determining regions having the following amino acid sequences: SEQ ID NO: 3; SEQ ID NO: 4; SEQ ID NO: 5; SEQ ID NO: 8; SEQ ID NO: 9; and SEQ ID NO: 10.

16. The method of claim 15, wherein the antibody is an antibody fragment selected from the group consisting of a Fab, Fab', F(ab)2, F(ab')2, scFv, and combinations thereof.

17. An antibody that specifically binds to human C5a, wherein the antibody has a heavy chain variable (VH) region and a light chain variable (VL) region, wherein the VH region has an amino acid sequence set forth in SEQ ID NO: 2, and wherein the VL region has an amino acid sequence set forth in SEQ ID NO: 7.

18. The antibody of claim 17, wherein the antibody is an antibody fragment selected from the group consisting of a Fab, Fab', F(ab)2, F(ab')2, scFv, and combinations thereof.

* * * * *

UNITED STATES PATENT AND TRADEMARK OFFICE

CERTIFICATE OF CORRECTION

PATENT NO. : 11,274,146 B2
APPLICATION NO. : 16/495979
DATED : March 15, 2022
INVENTOR(S) : Wenchao Song et al.

It is certified that error appears in the above-identified patent and that said Letters Patent is hereby corrected as shown below:

In the Specification

Column 1, Lines 14-20 should read as follows:
STATEMENT REGARDING FEDERALLY SPONSORED RESEARCH OR DEVELOPMENT
This invention was made with government support under AI044970 awarded by the National Institutes of Health. The government has certain rights in the invention.

Signed and Sealed this
Twenty-seventh Day of June, 2023

Katherine Kelly Vidal

Katherine Kelly Vidal
*Director of the United States Patent and Trademark Office*

SEQUENCE LISTING

```
<160> NUMBER OF SEQ ID NOS: 17

<210> SEQ ID NO 1
<211> LENGTH: 499
<212> TYPE: DNA
<213> ORGANISM: Mus musculus

<400> SEQUENCE: 1
```

```
catggactga aggagtagaa atcttcagtc cctgaacaca ctgactgtaa caatggaatg     60

gagctgggtc tctctcttct tcctgtcagt aactacaggt gtccactccc aggttcagct    120

gcaacagtct gacgctgagt tggtgaaacc tggagcttca gtgaagattt cctgcaaggt    180

ttctggctac accttcactg accatattat tcactggatg aaccagaggc ctgaacaggg    240

cctggaatgg attggatata tttatcctag agatggtaat actaactaca atgaaaactt    300

caagggcaag gccacattga ctgcagacaa atcctccagc acagcctaca tgcagctcaa    360

cagcctgaca tctgaggact ctgcagtcta tttctgtgca agagaaagga acttggaata    420

ctttgactac tggggccaag gcaccactct cacagtctcc tcagccaaaa cgacaccccc    480

atctgtctat ccactggcc                                                 499
```

```
<210> SEQ ID NO 2
<211> LENGTH: 149
<212> TYPE: PRT
<213> ORGANISM: Mus musculus

<400> SEQUENCE: 2

Met Glu Trp Ser Trp Val Ser Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Val Ser Gly Tyr Thr Phe
        35                  40                  45

Thr Asp His Ile Ile His Trp Met Asn Gln Arg Pro Glu Gln Gly Leu
    50                  55                  60

Glu Trp Ile Gly Tyr Ile Tyr Pro Arg Asp Gly Asn Thr Asn Tyr Asn
65                  70                  75                  80

Glu Asn Phe Lys Gly Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Ala Arg Glu Arg Asn Leu Glu Tyr Phe Asp Tyr Trp Gly
        115                 120                 125

Gln Gly Thr Thr Leu Thr Val Ser Ser Ala Lys Thr Thr Pro Pro Ser
    130                 135                 140

Val Tyr Pro Leu Ala
145
```

```
<210> SEQ ID NO 3
<211> LENGTH: 9
<212> TYPE: PRT
<213> ORGANISM: Mus musculus

<400> SEQUENCE: 3

Tyr Thr Phe Thr Asp His Ile Ile His
1               5
```

```
<210> SEQ ID NO 4
<211> LENGTH: 14
<212> TYPE: PRT
<213> ORGANISM: Mus musculus

<400> SEQUENCE: 4

Trp Ile Gly Tyr Ile Tyr Pro Arg Asp Gly Asn Thr Asn Tyr
1               5                   10
```

-continued

<210> SEQ ID NO 5
<211> LENGTH: 8
<212> TYPE: PRT
<213> ORGANISM: Mus musculus

<400> SEQUENCE: 5

```
Arg Asn Leu Glu Tyr Phe Asp Tyr
1               5
```

<210> SEQ ID NO 6
<211> LENGTH: 459
<212> TYPE: DNA
<213> ORGANISM: Mus musculus

<400> SEQUENCE: 6

```
catggactga aggagtagaa aaagcatcct ctcatctagt tctcagagat ggagacagac     60

acaatcctgc tatgggtgct gctgctctgg gttccaggct ccactggtga cattgtgctg    120

acccaatctc cagcttcttt ggctgtgtct ctagggcaga gggccaccat ctcctgcaag    180

gccagccaaa gtgttgatta tgatggtgat aattatatga actggtacca acagaaacca    240

ggacagccac ccaaactcct catctatgct gcatccaatc tagattctgg gatcccagcc    300

aggtttagtg gcagtgggtc tgggacagac ttcaccctca acatccatcc tgtggaggaa    360

gaagatgctg caacctatta ttgtcagcaa agtaatgagg atccgtacac gttcggaggg    420

gggaccaagc tggaaataaa acgggctgat gctgcacca                           459
```

<210> SEQ ID NO 7
<211> LENGTH: 137
<212> TYPE: PRT
<213> ORGANISM: Mus musculus

<400> SEQUENCE: 7

```
Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Asn Tyr Met Asn Trp Tyr Gln Gln Lys Pro
    50                  55                  60

Gly Gln Pro Pro Lys Leu Leu Ile Tyr Ala Ala Ser Asn Leu Asp Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Tyr Thr Phe Gly Gly Gly Thr Lys Leu
        115                 120                 125

Glu Ile Lys Arg Ala Asp Ala Ala Pro
    130                 135
```

<210> SEQ ID NO 8
<211> LENGTH: 12
<212> TYPE: PRT
<213> ORGANISM: Mus musculus

<400> SEQUENCE: 8

```
Gln Ser Val Asp Tyr Asp Gly Asp Asn Tyr Met Asn
```

1 5 10

<210> SEQ ID NO 9
<211> LENGTH: 11
<212> TYPE: PRT
<213> ORGANISM: Mus musculus

<400> SEQUENCE: 9

Leu Leu Ile Tyr Ala Ala Ser Asn Leu Asp Ser
1 5 10

<210> SEQ ID NO 10
<211> LENGTH: 8
<212> TYPE: PRT
<213> ORGANISM: Mus musculus

<400> SEQUENCE: 10

Gln Gln Ser Asn Glu Asp Pro Tyr
1 5

<210> SEQ ID NO 11
<211> LENGTH: 23
<212> TYPE: DNA
<213> ORGANISM: Mus musculus

<400> SEQUENCE: 11
gaggtgaagc tggtggagtc tgg 23

<210> SEQ ID NO 12
<211> LENGTH: 17
<212> TYPE: DNA
<213> ORGANISM: Mus musculus

<400> SEQUENCE: 12
ggggccagtg gatagac 17

<210> SEQ ID NO 13
<211> LENGTH: 32
<212> TYPE: DNA
<213> ORGANISM: Mus musculus

<400> SEQUENCE: 13
ccagttccga gctccagatg acccagactc ca 32

<210> SEQ ID NO 14
<211> LENGTH: 32
<212> TYPE: DNA
<213> ORGANISM: Mus musculus

<400> SEQUENCE: 14
ccagttccga gctcgtgctc acccagtctc ca 32

<210> SEQ ID NO 15
<211> LENGTH: 32
<212> TYPE: DNA
<213> ORGANISM: Mus musculus

<400> SEQUENCE: 15
ccagttccga gctccagatg acccagtctc ca 32

<210> SEQ ID NO 16
<211> LENGTH: 32
<212> TYPE: DNA
<213> ORGANISM: Mus musculus -continued

```
<400> SEQUENCE: 16

ccagttccga gctcgtgatg acacagtctc ca                              32


<210> SEQ ID NO 17
<211> LENGTH: 17
<212> TYPE: DNA
<213> ORGANISM: Mus musculus

<400> SEQUENCE: 17

gttggtgcag catcagc                                               17
```